United States Patent [19]

Acker et al.

[11] Patent Number: 5,558,091

[45] Date of Patent: Sep. 24, 1996

[54] MAGNETIC DETERMINATION OF POSITION AND ORIENTATION

[75] Inventors: David E. Acker, Setauket, N.Y.; Ian McNulty, Naperville, Ill.; Robert C. Pacheco, New York; Wayne Grandner, Port Jefferson Station, both of N.Y.

[73] Assignee: Biosense, Inc., Orangeburg, N.Y.

[21] Appl. No.: 132,479

[22] Filed: Oct. 6, 1993

[51] Int. Cl.⁶ ........................................................ A61B 5/05
[52] U.S. Cl. ................. 128/653.1; 128/899; 324/207.11; 324/207.13; 324/207.22; 364/460; 340/686
[58] Field of Search ................................. 128/653.1, 654, 128/897, 899, 903, 656, 658; 324/207.17, 207.11, 207.13, 207.22; 342/459, 359; 340/686; 364/449, 460

[56] References Cited

U.S. PATENT DOCUMENTS

| | | |
|---|---|---|
| 3,847,157 | 11/1974 | Caillouette et al. . |
| 3,872,858 | 3/1975 | Hudson et al. . |
| 4,054,881 | 10/1977 | Raab . |
| 4,173,228 | 11/1979 | Van Steenwyk et al. . |
| 4,223,228 | 9/1980 | Kaplan . |
| 4,317,078 | 2/1982 | Weed et al. . |
| 4,328,548 | 5/1982 | Crow et al. ............................. 364/460 |
| 4,375,818 | 3/1983 | Suwaki et al. . |
| 4,396,885 | 8/1983 | Constant . |
| 4,422,041 | 12/1983 | Lienau . |
| 4,431,005 | 2/1984 | McCormick . |
| 4,494,549 | 1/1985 | Namba et al. . |
| 4,572,198 | 2/1986 | Codrington ............................. 128/658 |
| 4,613,866 | 9/1986 | Blood . |
| 4,642,796 | 2/1987 | Hansen . |
| 4,652,820 | 3/1987 | Maresca . |
| 4,661,773 | 4/1987 | Kawakita et al. . |
| 4,697,595 | 10/1987 | Breyer et al. . |
| 4,710,708 | 12/1987 | Rorden et al. . |
| 4,829,250 | 5/1989 | Rotier . |
| 4,831,330 | 5/1989 | Takahashi ............................. 324/318 |
| 4,849,692 | 7/1989 | Blood . |
| 4,880,011 | 11/1989 | Imade et al. . |
| 4,905,698 | 3/1990 | Strohl, Jr. et al. . |
| 4,932,411 | 6/1990 | Fritschy et al. . |
| 4,936,307 | 6/1990 | Saito et al. . |
| 4,945,305 | 7/1990 | Blood . |
| 4,945,914 | 8/1990 | Allen ..................................... 128/653.1 |
| 4,951,677 | 8/1990 | Crowley et al. . |
| 4,960,106 | 10/1990 | Kubokawa et al. ......................... 128/6 |
| 4,989,608 | 2/1991 | Ratner . |
| 4,993,404 | 2/1991 | Lane . |
| 4,998,282 | 3/1991 | Shishido et al. . |
| 5,005,592 | 4/1991 | Cartmell ................................. 128/899 |

(List continued on next page.)

FOREIGN PATENT DOCUMENTS

| | | |
|---|---|---|
| 0061332 | 3/1982 | European Pat. Off. . |
| 2417970 | 2/1979 | France . |
| 3-48 | 4/1991 | Japan . |
| 2094590 | 2/1982 | United Kingdom . |

OTHER PUBLICATIONS

IEEE Transactions On Biomedical Engineering, vol. BME-31, No. 4, Apr. 1984.
"An Inexpensive Eye Movement Monitor Using The Scleral Search Coil Technique" By Ronald S. Remmel; Ultrasonically Marked Catheter—A Method For Positive Echographic Catheter Position Identification By B. Breyer (IFMBE: 1984).

*Primary Examiner*—Krista M. Zele
*Assistant Examiner*—Brian L. Casler
*Attorney, Agent, or Firm*—Lerner, David, Littenberg, Krumholz & Mentlik

[57] ABSTRACT

A magnetic position and orientation determining system uses magnetic fields, desirably including uniform fields from Helmholtz coils positioned on opposite sides of a sensing volume and gradient fields generated by the same coils. By monitoring field components detected at the probes during application of these fields, the position and orientation of the probe in the field can be deduced. A representation of the probe can be superposed on a separately acquired image of the subject to show the position and orientation of the probe with respect to the subject.

45 Claims, 6 Drawing Sheets

U.S. PATENT DOCUMENTS

| | | |
|---|---|---|
| 5,020,539 | 6/1991 | Yokoi et al. . |
| 5,042,486 | 8/1991 | Pfeiler et al. . |
| 5,047,715 | 9/1991 | Morgenstern . |
| 5,054,491 | 10/1991 | Saito et al. . |
| 5,070,462 | 12/1991 | Chau . |
| 5,073,858 | 12/1991 | Mills ................................ 128/653.1 |
| 5,078,714 | 1/1992 | Katims . |
| 5,099,845 | 3/1992 | Besz et al. ............................ 128/899 |
| 5,109,194 | 4/1992 | Cantaloube . |
| 5,168,222 | 12/1992 | Voisin et al. . |
| 5,170,789 | 12/1992 | Narayan et al. ..................... 128/653.5 |
| 5,172,056 | 12/1992 | Voisin . |
| 5,186,174 | 2/1993 | Schlondorff et al. . |
| 5,206,589 | 4/1993 | Kado et al. . |
| 5,211,165 | 5/1993 | Dumoulin et al. . |
| 5,218,174 | 6/1993 | Gray et al. . |
| 5,251,635 | 10/1993 | Dumoulin et al. . |
| 5,253,647 | 10/1993 | Takahashi et al. .................. 128/653.1 |
| 5,255,680 | 10/1993 | Darrow et al. . |
| 5,257,636 | 11/1993 | White ................................. 128/653.1 |
| 5,265,610 | 11/1993 | Darrow et al. . |
| 5,271,400 | 12/1993 | Dumoulin et al. . |
| 5,273,025 | 12/1993 | Sakiyama et al. ..................... 128/899 |
| 5,285,785 | 2/1994 | Meyer . |
| 5,285,787 | 2/1994 | Machida . |
| 5,309,913 | 5/1994 | Kormos et al. . |
| 5,316,024 | 5/1994 | Hirschi et al. ......................... 128/658 |
| 5,318,025 | 6/1994 | Dumoulin et al. ..................... 128/658 |
| 5,325,873 | 7/1994 | Hirschi et al. ....................... 128/653.1 |
| 5,353,795 | 10/1994 | Souza et al. .......................... 128/658 |
| 5,383,454 | 1/1995 | Bucholz . |
| 5,391,199 | 2/1995 | Ben-Haim . |
| 5,425,367 | 6/1995 | Shapiro et al. ..................... 128/653.1 |
| 5,425,382 | 6/1995 | Golden et al. ......................... 128/899 |
| 5,429,132 | 7/1995 | Guy et al. .......................... 128/653.1 |
| 5,434,500 | 7/1995 | Hauck et al. ....................... 324/207.17 |

MAGNETIC DETERMINATION OF POSITION AND ORIENTATION

BACKGROUND OF THE INVENTION

The present invention relates to apparatus and methods for determining the position and orientation of an object by means of magnetic fields, and includes apparatus and methods for monitoring the position of a probe within the body of a medical patient by means of magnetic fields.

Various methods have been utilized for determining the position and orientation of an object in space. For example, it is often necessary to determine the position and orientation of a medical instrument within the body of a patient as, for example, to monitor the position and orientation of a catheter, endoscope or other probe. It is desirable to present data showing the object superposed on a picture of the patient such as on an image showing internal organs. One simple method of accomplishing this is to take a direct X-ray image, such as a fluoroscopic image, showing both the patient and the inserted probe. This method has the disadvantage that the entire imaging procedure to acquire an image of the patient must be repeated whenever the probe is moved. X-ray imaging such as fluoroscopy can be performed during some surgical procedures, but inherently expose the patient to unwanted ionizing radiation. Some types of imaging procedures, such as MRI imaging cannot be repeated during surgery or other treatment procedures.

As illustrated for example in GB patent application 2,094,590 and in U.S. Pat. No. 5,186,174, the probe may be mechanically constrained or linked to an arm or frame so that the position of the probe is constrained with respect to a fixed frame of reference and known with respect to that frame of reference. An image of the probe may be superposed on an image of the patient, using the positional data derived from the fixed frame of reference. However, these systems make the probe inflexible and hence impose severe disadvantages in the medical procedure itself. For example, one such system requires that a probe be advanced in a straight line to the area of interest. Systems of this nature are more suitable for positioning a probe on the outside of the body than inside the body.

Bryer et al. U.S. Pat. No. 4,697,595 and Bryer et al., Ultrasonically Marked Catheter—a Method for Positive Echographic Catheter Position Identification, *Medical and Biological Engineering and Computer*, vol. 22, No. 3 (1984), pp. 268–271, both disclose intracardiac catheters equipped with ultrasonic detectors. The position of the catheter is deduced from time of flight measurements from an ultrasonic transducer on the exterior of the patient to the catheter, and the deduced position is superimposed on an ultrasonically generated image.

Van Steenwyk et al. U.S. Pat. No. 4,173,228; Pfeiler et al. U.S. Pat. No. 5,042,486 and Dumoulin et al. U.S. Pat. No. 5,211,165 all disclose arrangements wherein electromagnetic signals are propagated between one antenna on the tip of a medical catheter inserted in the body and several antennas outside of the body. The position and orientation of the catheter tip are assertedly determined from the signals transmitted between these antennas. That is, the relative position and orientation is deduced from the properties of the signal propagation path between these antennas as, for example, from the degree of signal attenuation in transit from one antenna to the others. The Van Steenwyck patent notes the possibility of using a magnetic field and a Hall effect transducer sensor, but offers no details as to how this might. be accomplished in a practical device. Dumoulin suggests that the radio frequency derived position of a catheter tip can be superposed on an image acquired by an imaging system.

Numerous systems have been proposed for locating articles outside of the human body by use of magnetic fields. Thus Blood, U.S. Pat. Nos. 4,945,305; 4,849,692 and 4,613,866 all disclose systems for determining the position and orientation of objects in three-dimensional space using magnetic coils on the object to be located and stationary coils in a fixed frame of reference. Other systems of this type include Voisin U.S. Pat. Nos. 5,172,056 and 5,168,222; Constant U.S. Pat. No. 4,396,885; Cantaloube U.S. Pat. No. 5,109,194; Weed et al. U.S. Pat. No. 4,317,078; Hansen U.S. Pat. No. 4,642,786 and Morgenstern U.S. Pat. No. 5,047,715. These systems typically employ a magnetic field transmitter incorporating several coils wound on orthogonal axes about an iron core, and a similar structure used as a receiver. The coils of the transmitter are actuated in sequence and/or at different frequencies, and the signals detected by the coils of the receiver are analyzed to determine the position and orientation of the transmitter relative to the receiver. Among the uses for such systems are three-dimensional data entry devices for computers and systems for detecting the position and orientation of a helmet.

Additionally, as disclosed in Remel, An Inexpensive Eye Movement Monitor Using the Scleral Search Coil Technique, IEEE Transactions On Biomedical Engineering, vol. BME-34, #4 April 1984, pp 388–390, researchers attempting to follow the rotation of the eyeball have mounted small loop-like sensing coils on the surface of the eyeball, as by suturing or by incorporating the coil in a contact lens. The subject having such a coil is placed between pairs of orthogonally oriented Helmholtz coils which are energized with high-frequency alternating currents having two different frequencies. The voltage induced in the coil on the eye will include components at both frequencies, and the relative magnitudes of these components will depend upon the orientation of the eye.

Despite all of these efforts in the art, there still has been a need heretofore, for improved apparatus and methods for determining the position and orientation of an object in space, and, particularly, for improved apparatus and methods for determining the position and orientation of a probe within the body of a living subject.

SUMMARY OF THE

Certain aspects of the present invention provide apparatus and methods for determining the position and orientation of probes. Apparatus according to one aspect of the present invention, includes magnet means which are selectively operable to generate a plurality of different magnetic fields, each having at least one non-zero component with magnitude which is "quasilinear", i.e. constant, linear, or nearly linear, with respect to distance in a reference direction within a sensing volume. The apparatus further includes control means for actuating the magnet means to generate the different fields in a preselected sequence, and a sensor connected to the object to be monitored so that the sensor is moveable along with the object within the sensing volume. The sensor is arranged to detect magnetic field components in at least two different, preferably orthogonal, local directions relative to the sensor. Desirably, the sensor is arranged to detect magnetic field components in three different, desirably orthogonal, local directions relative to the sensor.

The local directions are directions in the frame of reference of the sensor, and usually differ from the reference directions of the magnet means. The apparatus further includes calculation means for determining the position and orientation of the sensor relative to the magnet means from the magnetic field components detected by the sensor while the magnet means are operated to generate the various magnetic fields.

Because the fields within the sensing volume have quasilinear components—either uniform or varying close to linearly with distance, appreciable, measurable fields and appreciable rates of variation in field component magnitudes per unit distance can be provided throughout a relatively large sensing volume as, for example, throughout a sensing volume having minimum dimensions of about 30 cm or more, even where the maximum field is relatively low. This allows accurate monitoring of orientation and position with a magnetic field sensor of reasonable sensitivity. This, in turn, permits the use of a very small sensor, preferably a solid-state sensor, which can be accommodated readily within the tip of a catheter, endoscope or other medical probe.

Desirably, the magnet means are arranged to generate a first substantially uniform magnetic field in a first reference direction within a sensing volume. The magnet means are also selectively operable to generate a second substantially uniform magnetic field in a second reference direction different from the first reference direction within the sensing volume. Preferably, the second reference direction is orthogonal to the first reference direction. The magnet means are also selectively operable to generate first and second gradient fields within the sensing volume, so that the first gradient field has a predetermined pattern of variation in the first references direction within the sensing volume. The second gradient field has a predetermined pattern of variation within the sensing volume, desirably a predetermined pattern of variation in the second reference direction.

Preferably, the magnet means is also operable to generate a field such that a component of the field varies with a predetermined pattern of variation in a third reference direction, different from, and preferably orthogonal to, the first and second reference directions, and the calculation means is arranged to determine the position of the probe in the third direction, as well as in the first and second directions. The component varying in the third direction may be provided as a part of a third gradient field different from the first and second gradient fields and from the uniform fields. Alternatively, the component varying in the third direction may be provided in the first gradient field, second gradient field or both. The magnet means may also be arranged to generate a third uniform field in the third reference direction.

Most preferably, the magnet means include a plurality of sets, each such set including a pair of field-directing elements disposed on opposite sides of the sensing volume. The field-directing elements may be arranged to direct flux codirectionally with one another to provide a substantially uniform field in the sensing volume and to direct flux counterdirectionally to one another to provide a gradient field in the sensing volume. The field-directing elements of each such pair desirably are electrically conductive coils, most preferably Helmholtz coils disposed substantially coaxially with one another so that the axis of each such pair extends in one of the reference directions.

Apparatus according to a further aspect of the invention includes a magnet structure including at least two pairs of Helmholtz coils, the coils of each such pair being substantially coaxial with one another and defining a pair axis. The coils of each such pair are disposed on opposite sides of a sensing volume so that the coil axes of the various pairs are substantially orthogonal to one another. The apparatus further includes control means for actuating each said pair of Helmholtz coils in a homogeneousfield state with codirectional current flow around the pair axis in both. coils of the pair to thereby generate a magnetic field directed parallel to the pair axis and having substantially uniform strength within the sensing volume. The control means is also operative to actuate each pair of Helmholtz coils in a gradient field state with counterdirectional current flow in the coils of the pair so as to generate a magnetic field having a component directed parallel to the pair axis, such component having a substantially linear gradient of magnitude in the sensing volume.

The control means desirably is operative to actuate the magnet structure so that the pairs of coils are actuated to different states according to a preselected time sequence, typically with only one pair actuated to only one state at any time. Apparatus according to this aspect of the invention preferably also includes a sensor moveable within the sensing volume, the sensor being arranged to measuring magnetic field components in at least two, and preferably three, mutually orthogonal local directions relative to the sensor. Thus, the sensor will measure homogeneous-field local components in the local directions while the coil pairs are in the aforementioned homogeneous-field states and the sensor will also measure gradient-field local components in the local directions relative to the sensor while the coil pairs are in the aforementioned gradient field states.

Apparatus according to this aspect of the invention also includes calculation means for determining the orientation of the sensor relative to the pair axes from the homogeneousfield local components and for determining the position of the sensor in the sensing volume from the homogeneousfield local components and the gradient field local components. Most preferably, the control means is arranged to bring the magnet means to an inactive condition in which the magnet means provides no field in the sensing volume, and the calculation means is arranged to register baseline values of the magnetic field components in the aforementioned local directions measured by the sensing means while the magnet means is in the off condition. Thus, the calculation means is arranged to correct the local component measured while the magnet means are in other conditions, as by subtracting the baseline values.

Desirably, the sensor used in the aforementioned apparatus incorporates magnetically sensitive elements having maximum dimensions less than about 5 mm and preferably less than about 1 mm. Most preferably, the entire sensor may have a length of about 3 mm or less and widthwise dimensions transverse to such length of about 0.75 mm or less. Stated another way, the sensor may fit inside a volume of 3.0 $mm^3$ or less, more desirably 2.0 $mm^3$ or less. Preferably, the sensor is mounted on a probe, such as a probe adapted for disposition within the body of a human patient, such as a catheter, endoscope or the like. For example, the probe may incorporate an elongated structure having a proximal end and a distal end, and the sensor may be mounted at the distal end so as to provide measurement of the position and orientation of the distal end when the distal end is inserted into the body.

The apparatus may further include superposition means for displaying an image of a patient's body with a representation of the probe superposed thereon so that the representation of the probe is superposed at a location on the image of the body corresponding to the location of the probe within the body. The superposition means may include means for accepting body image data representing the body image in a body image frame of reference different from the frame of reference defined by the reference directions of the magnet means, means for accepting relationship data representing the relationship between the body image frame of reference and the magnet means frame of reference and means for transforming the position of the probe in the magnet means frame of reference, the body image data or both, so as to provide the probe position data and the body image data in a common frame of reference. The apparatus may incorporate one or more fiducial markers, and means for attaching each said fiducial marker to the patient's body so that the image to be displayed by the superposition means will include an image of each fiducial marker. The apparatus may further include means for determining the position of each fiducial markers in the magnet means frame of reference. In a particularly preferred arrangement, each fiducial marker includes a sensor for measuring the magnetic field components, and the calculation means is arranged to determine the position and orientation of each fiducial marker from the magnetic fields measured by the sensors of the fiducial markers. Thus, the relationship data will include data regarding the difference, if any, between the position and orientation of each fiducial marker as derived from magnetic field measurements and the position and orientation of the fiducial marker as shown in the image data.

Further aspects of the invention provide methods of determining the position and orientation of a sensor within a sensing volume. Methods according to this aspect of the invention include the steps of generating a plurality of magnetic fields in a sensing volume, each including one or more quasilinear components as discussed above. Desirably, the plural magnetic fields include first and second homogeneous magnetic fields having non-zero components of substantially uniform magnitude throughout the sensing volume in first and second reference directions, and further include first and second gradient fields having components which vary in predetermined patterns of variation. As discussed above in connection with the apparatus, a sensor disposed within the sensing volume measures magnetic field components in at least two, and preferably three, different local directions relative to the sensor during application of each of these fields. The orientation of the probe relative to the reference directions of the homogeneous-fields is determined from the homogeneous-field local components measured by the sensor during application of the homogeneous fields, and the position of the probe in the reference directions of the gradient fields is determined from the homogeneous field local components and from the gradient field local components measured during application of the first and second gradient fields.

Methods according to this aspect of the present invention can provide benefits similar to those discussed above with reference to the apparatus. Most preferably, the methods include a step of stopping generation of all fields by the apparatus and actuating the sensor to detect components, such as from the earth's magnetic field, stray magnetic sources and the like. This baseline component data can be used to correct other data acquired by the sensor. Most preferably, the sensor is a small sensor as discussed above, mounted on a probe inserted in a living subject. The image of the probe may be superposed on an image of the subject, such as an X-ray, MRI or CAT image.

Further ,aspects of the invention provide methods of displaying the location of a monitoring probe in a living subject. Methods according to these aspects of the invention preferably include the steps of providing at least one fiducial marker in a fixed position relative to the subject and acquiring an image of the subject including a depiction of the fiducial marker. The methods further include the step of determining the location of each fiducial marker and of the monitoring probe in a common frame of reference by measuring magnetic fields transmitted to or from the fiducial marker and the monitoring probe, so that the position of the monitoring probe relative to the fiducial marker is known. Desirably, methods according to this aspect of the invention include the step of superposing a representation of the monitoring probe on the image of the subject at a position relative to the depiction of the fiducial marker corresponding to the position of the monitoring probe relative to the fiducial marker, as determined by means of the magnetic fields. These methods may further include the steps of determining the orientation of the monitoring probe and of the fiducial marker in a common frame of reference in the magnetic fields and orienting the superposed representation of the monitoring probe on the image of the subject, accordingly, so that the orientation of the monitoring probe representation relative to the depiction of the reference probe in the superposed images corresponds to the true orientation of the monitoring probe relative to the reference probe.

A further aspect of the invention provides a method of depicting an element present in a surgical or medical procedure, such as a body part, a surgical instrument or the like. Methods according to this aspect of the invention include the steps of providing a sensor in a substantially fixed position relative to the element and acquiring an image of the element while the element is in a first orientation. The method further includes the step of monitoring the orientation of the probe by monitoring magnetic fields transmitted to or from the probe, to thereby monitor the orientation of the element when the element is in a moved orientation different from the first orientation. The method further includes the step of transforming the image of the element in the first orientation into an image of the element in its moved orientation and displaying the transformed image. Preferably, the monitoring, transforming and displaying steps are repeated as the element is moved through a range of moved orientations so that a transformed image corresponding to each such moved orientation is displayed substantially in real time when the element is in such moved orientation.

The method may be performed with a plurality of elements simultaneously. Thus, separate sensors may be affixed to each of a plurality of elements, and the steps of acquiring an image of the element may include the step of acquiring the images of all of the elements in respective first positions. The steps of monitoring the orientation of the sensor and determining the orientation of the element may include the step of monitoring the orientation of all of the sensors and determining separate moved orientations for each element. The step of transforming the image may include the step of transforming the image of each element into an image of that element in its respective moved orientation. The displaying step may be conducted so as to display all of the transformed images together, so that the orientations of the transformed images relative to one another correspond to the orientations of the elements relative to one another. For example, where the elements are the bones connected to one another at a skeletal joint, the physician can observe the transformed images of the bones, and thus observe the relative orientations of the elements constituting the joint during a medical procedure without taking additional x-rays as the bones are moved.

Preferably, the method includes the step of determining the position of each sensor in a fixed frame of reference while the elements are in their respective starting orientations and while the elements are in the respective moved orientations, so that the steps of transforming and displaying the images may include the step of adjusting the positions of the displayed transformed images relative to one another to compensate for relative movement of the elements. Thus, the displayed images will correctly represent the positions of the elements relative to one another.

Yet another aspect of the invention includes methods of mapping physiologic variables within the body of a living subject. A method according to this aspect of the invention desirably includes the steps of placing a probe in or on the body, sensing a physiologic variable by means of a transducer element on the probe and determining the position of the probe by monitoring magnetic fields directed to or from a magnetic field sensor on the probe to thereby provide a measurement of the physiologic variable associated with a position. Most preferably, methods according to this aspect of the invention include the further steps of repeating the aforesaid steps to provide a plurality of measurements associated with a plurality of positions, to thereby provide a map of the physiologic variable over a plurality of positions. The method may further include the step of displaying such map as a visible image as, for example, as a set of contour lines, areas of different color or areas of differing contrast, with or without other features derived from other imaging modalities. For example, a map of body temperature, oxygen level or other physiologic variable can be overlaid on an MRI, CAT or similar image.

Still further aspects of the invention provide apparatus including means for generating one or more magnetic fields in a field frame of reference so that at least one of the magnetic fields so generated has at least one non-zero parameter which is quasilinear with respect to distance from point to point within the field frame of reference. The apparatus according to this aspect of the invention further includes a probe adapted for disposition within the patient's body, a sensor mounted on the probe for monitoring the magnetic field prevailing at the probe while the probe is disposed in the patient's body and for sending a signal representing at least one parameter of the so-monitored field. The apparatus desirably further includes calculation means for determining the position of the probe in the field frame of reference from the signal provided by the field sensor means while the probe is disposed in the patient's body. The apparatus may also include superposition means for displaying an image of the patient's body with a representation of the probe so that the representation of the probe is superposed on the displayed image at a location on the body image conforming to the probe position data provided by the calculation means. Desirably, the probe includes an elongated structure heading a proximal end and a distal end, and the magnetic field sensor means is operative to monitor the magnetic field prevailing at the distal end of the elongated structure. Such apparatus can be used, for example in endoscopic procedures including endoscopic surgical procedures. Still further aspects of the invention include methods of operating apparatus as aforementioned.

Still further aspects of the present invention provide magnetic sensors, and combined magnetic and physiologic sensors, and methods of making the same. A sensor according to this aspect of the invention may include a sheetlike support and a plurality of magnetically sensitive elements, each having a preselected sensitive direction, disposed on the support. The support is folded so that the magnetically sensitive elements are non-coplanar. The support may incorporate a rectangular or square central panel with two side panels, a tip panel and an elongated strip all extending from different edges of the central panel to form a generally cruciform shape. The sensitive elements may be mounted on the various panels, and the panels may be folded over a dielectric core. The sensor most preferably incorporates a physiologic sensing element sensitive to a physiologic variable, this sensing element being attached to the same support as the magnetically sensitive elements. The entire device can be extremely compact.

The foregoing and other objects, features and advantages of the present invention will be more readily apparent from the detailed description of the preferred embodiments set forth below, taken in conjunction with the accompanying drawings.

Figure 1:
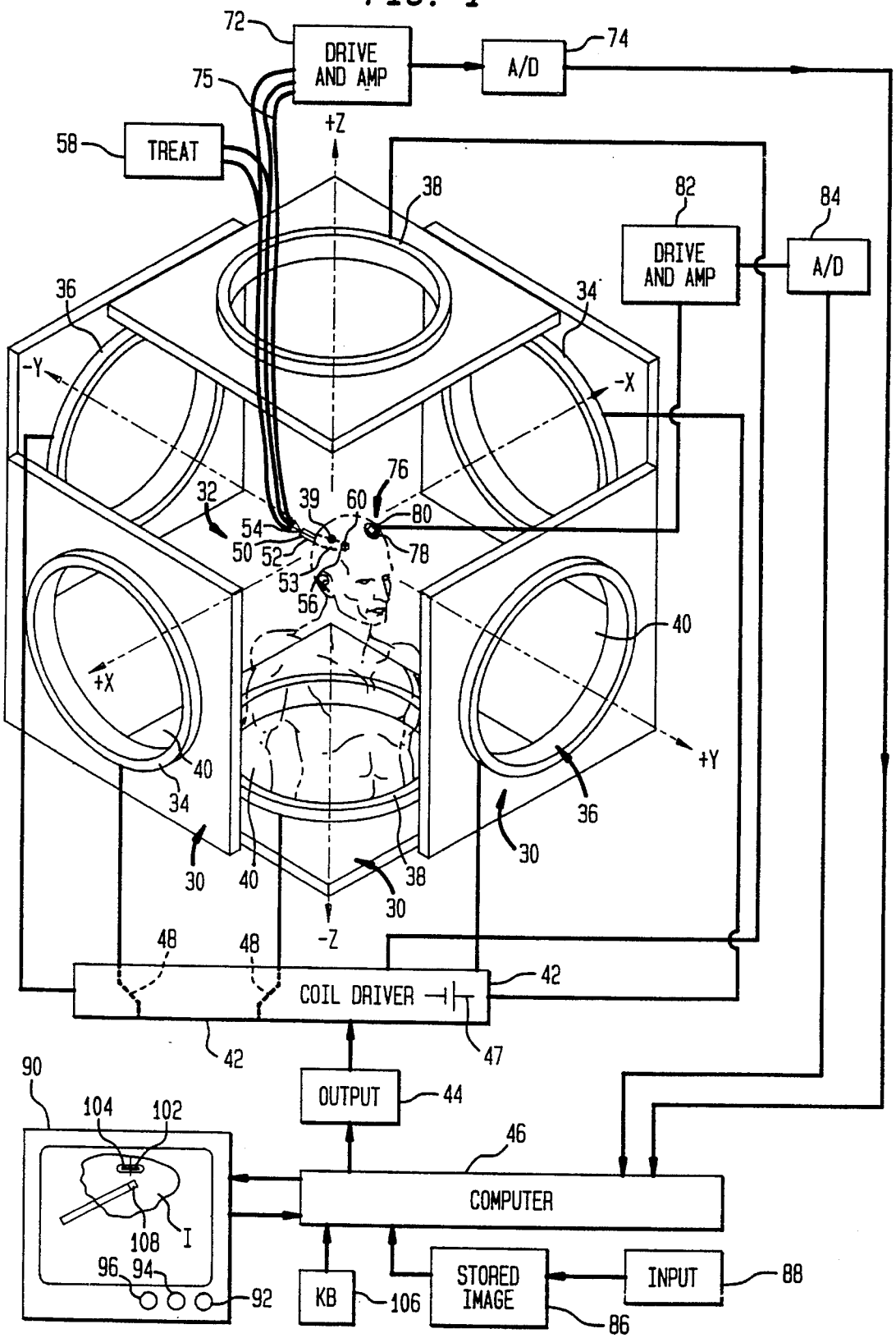
FIG. 1 is a diagrammatic, partially prospective view of apparatus in accordance with one embodiment of the invention.
Figure 2:
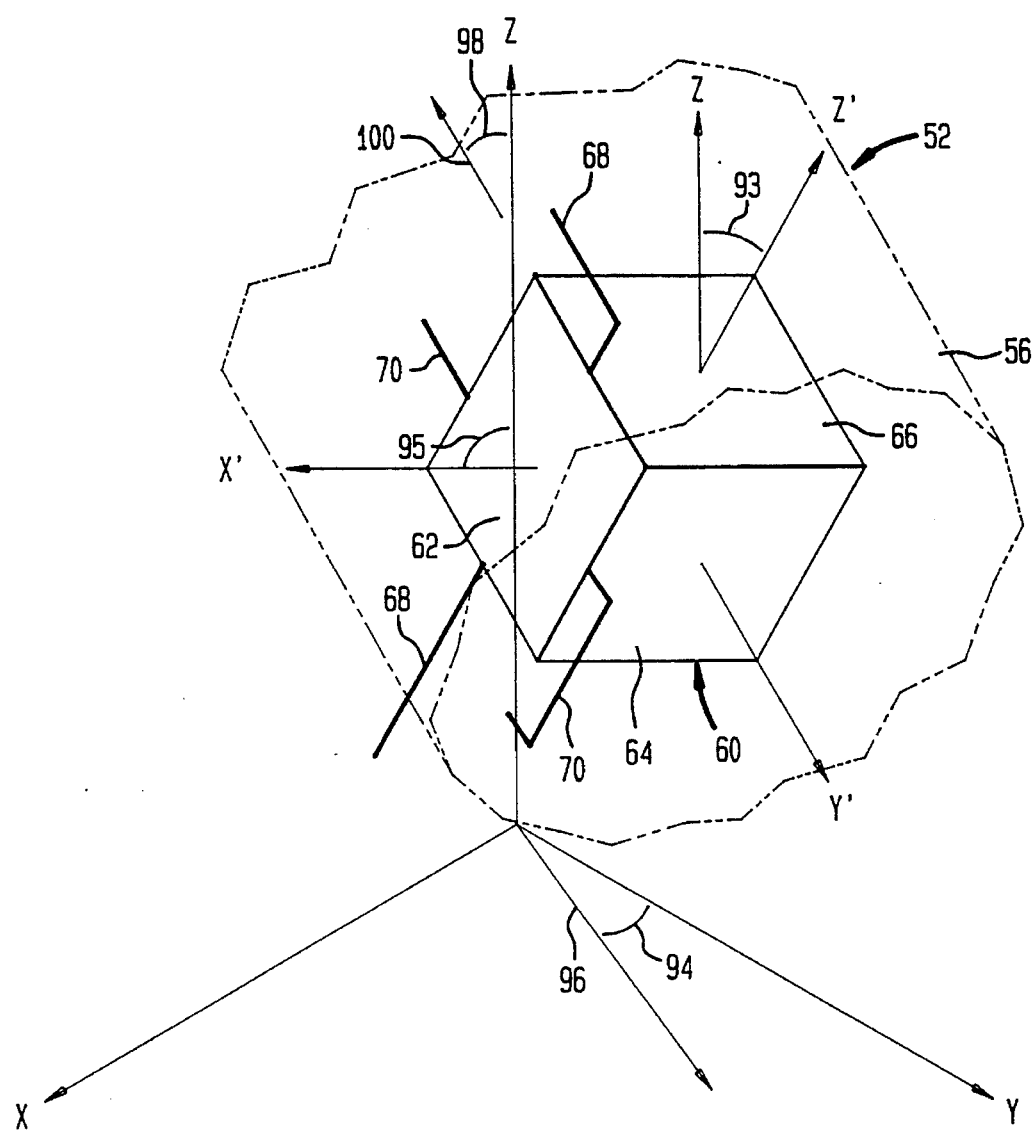
FIG. 2 is a diagrammatic view depicting a portion of the apparatus illustrated in FIG. 1.
Figure 3:
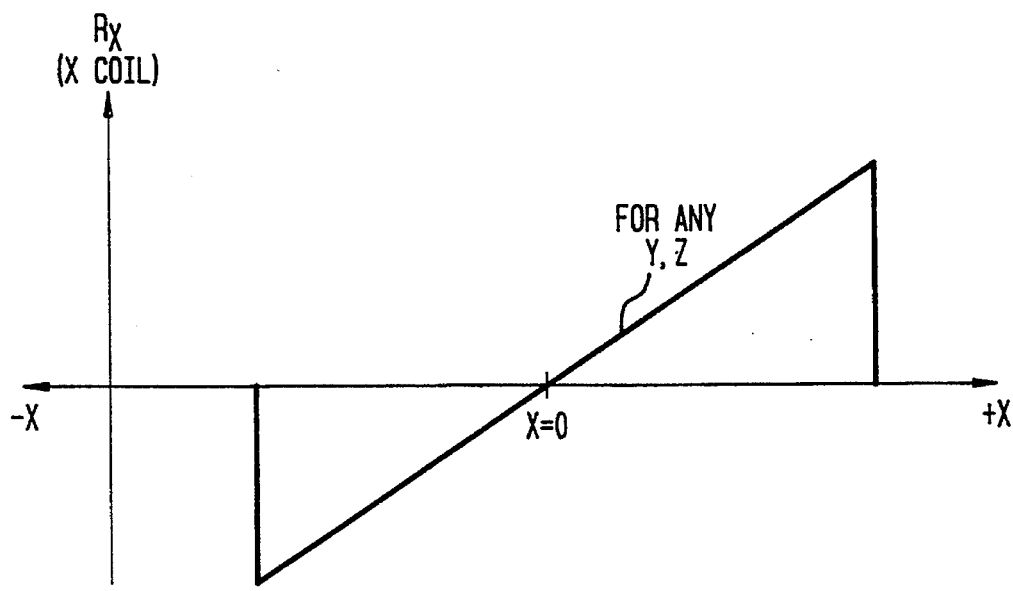
Figure 4:
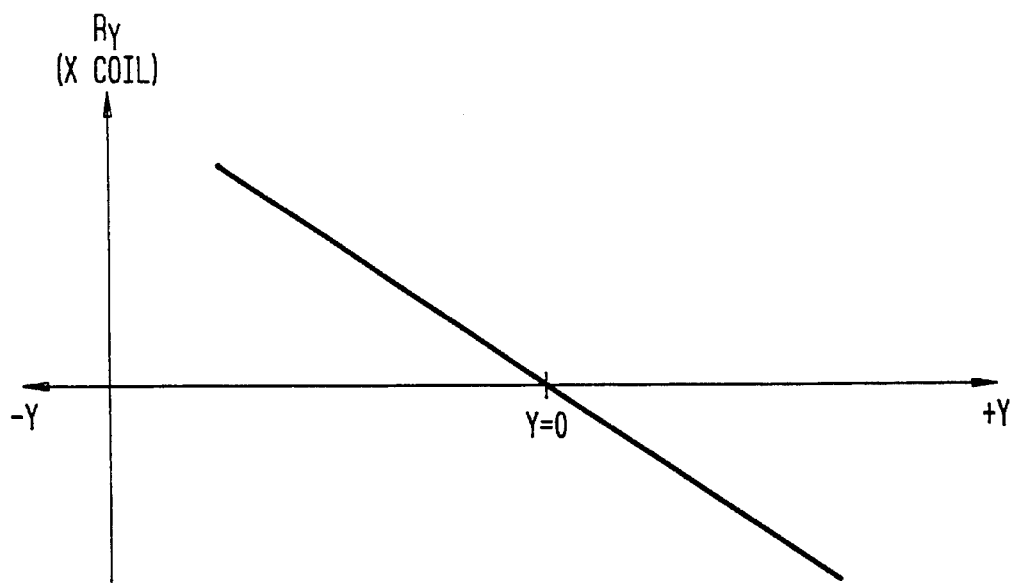
Figure 5:
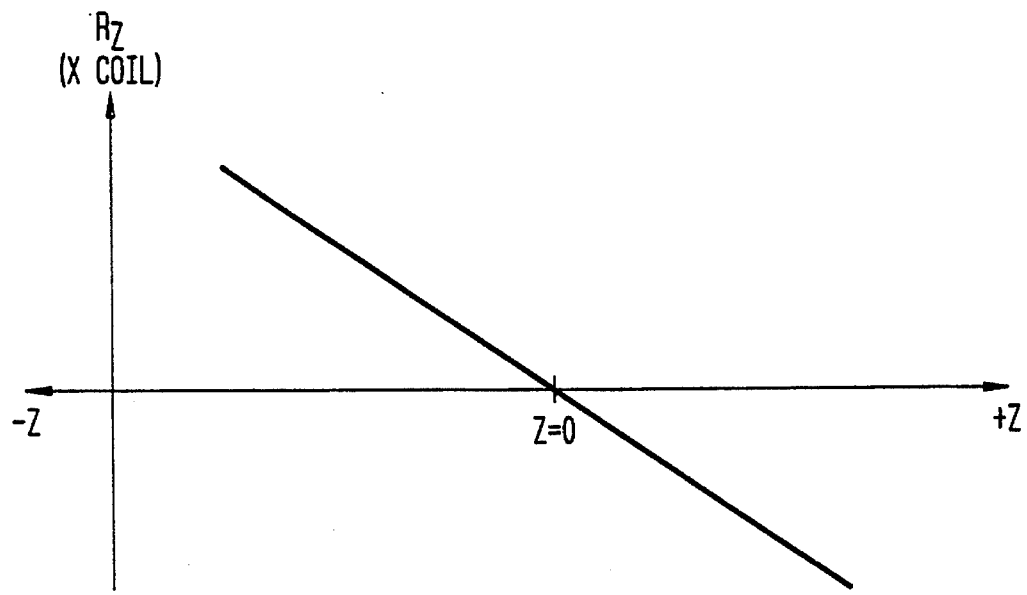

Each of FIGS. 3–5 is a graph illustrating certain magnetic fields occurring in the apparatus of FIG. 1–2.

Figure 6:
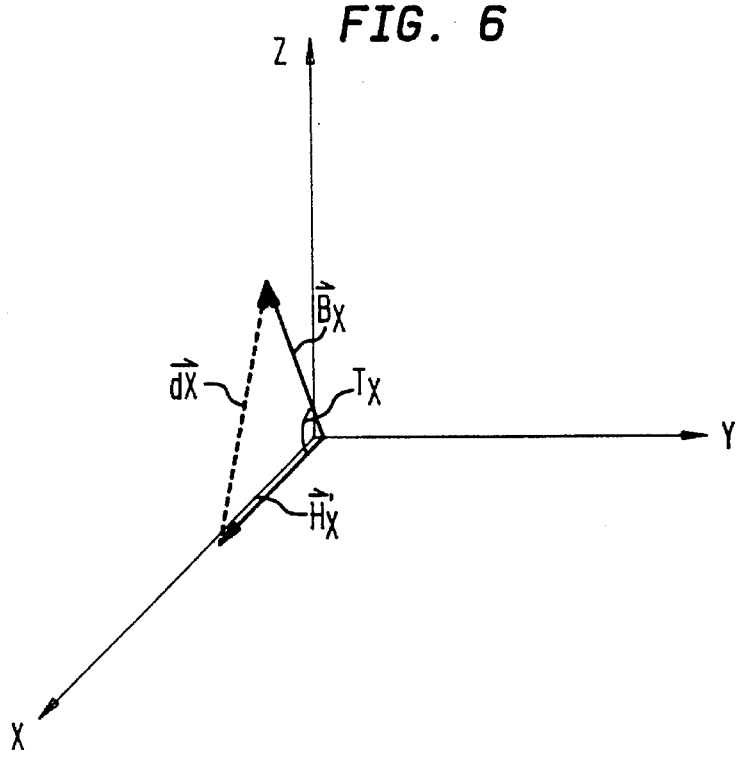

FIG. 6 is a vector diagram relating to operation of the apparatus of FIGS. 1–2.

Figure 7:
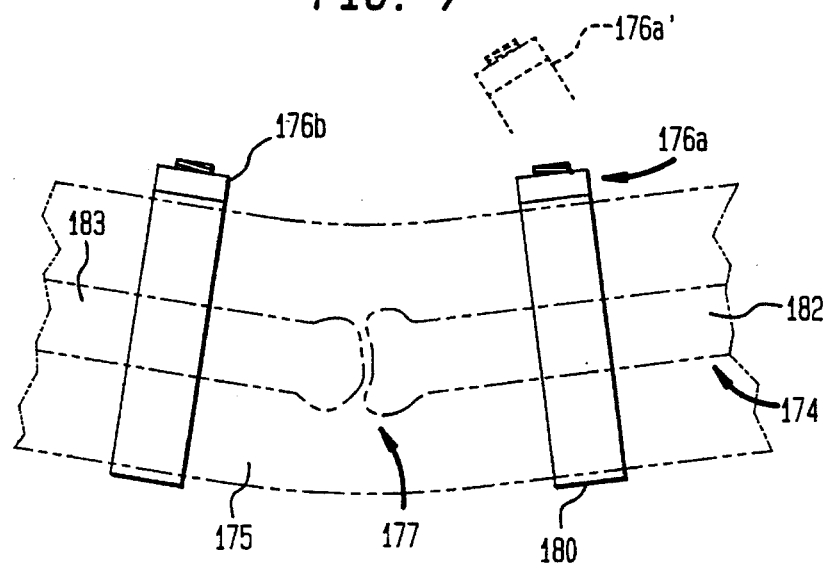
Figure 8:
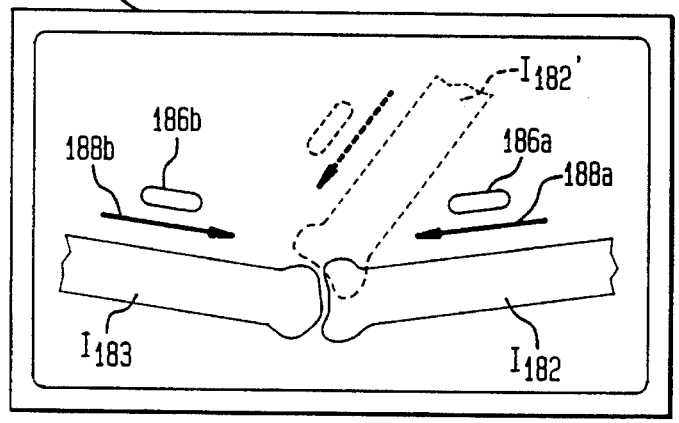

FIGS. 7 and 8 are fragmentary diagrammatic elevational views depicting portions of apparatus in accordance with another embodiment of the invention.

Figure 9:
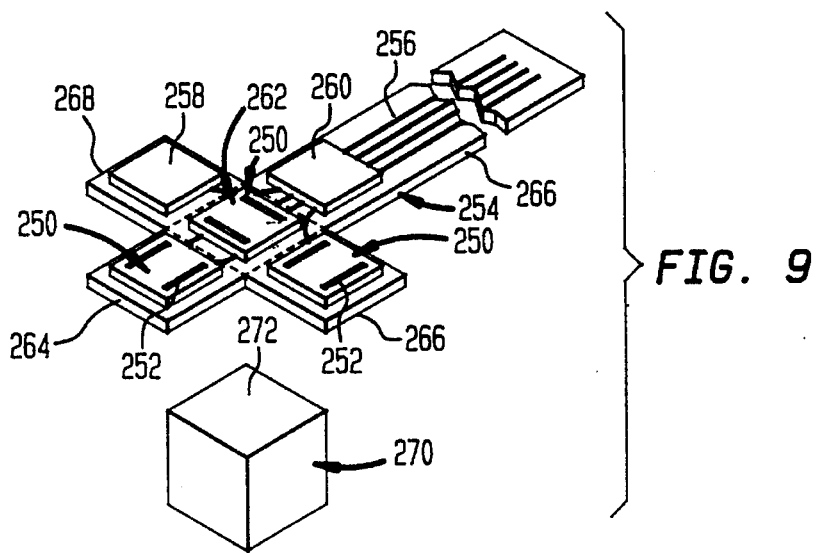

FIG. 9 is a fragmentary perspective view depicting a portion of apparatus in accordance with yet another embodiment of the invention.

Figure 10:
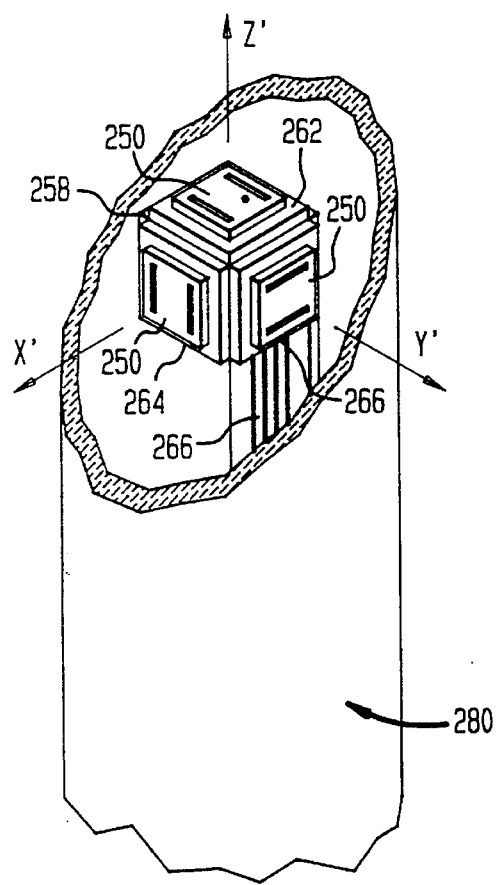

FIG. 10 is a fragmentary elevational view depicting another portion of the apparatus of FIG. 9.

Figure 11:
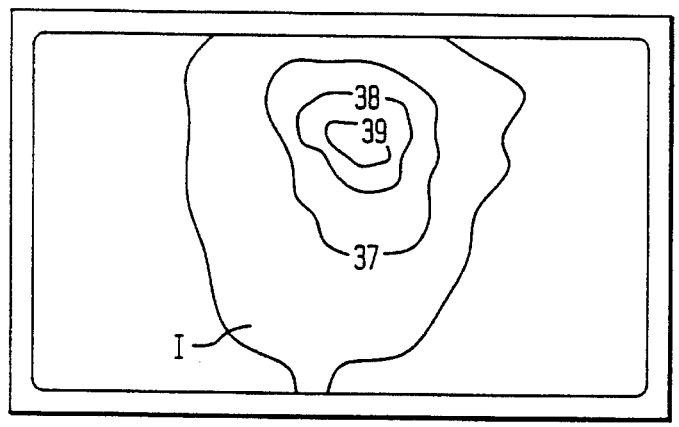

FIG. 11 is a view depicting temperatures measured by the probed as contour lines over laid on the body image.

DETAILED DESCRIPTION OF THE PREFERRED EMBODIMENTS

Apparatus in accordance with one embodiment of the invention includes a frame structure 30 substantially surrounding a sensing or patient receiving volume 32. Frame structure 30 supports three pairs of Helmholtz coils 34, 36 and 38 so that the coils of each pair are disposed coaxially with one another on three mutually orthogonal pair axes X, Y and Z. The intersecting pair axes thus form a conventional Cartesian coordinate system having an origin 39 at the center of the sensing volume and having positive and negative directions from the origin along each of the X, Y and Z axes. The coils of each pair are disposed on opposite sides of the sensing volume 32. All of the coils are circular, of equal diameter and have equal numbers of turns. The two coils of each pair are wound co-directionally with one another. Thus, both coils 34 arranged along the X axes have windings which wrap around the X axes in a right-handed or counterclockwise direction as seen from the positive end of the X axis. The spacings between the coils are exaggerated for clarity of illustration in FIG. 1. Preferably, the distance between the coils of the pair as measured along the axes of the pair is between about 0.5 and about 1.4 times the diameter of each coil. Rules for design of Helmholtz coils to provide uniform fields and to provide fields having substantially linear gradients are set forth in the article "Modifying Helmholtz Coils to Magnetically Drive a Small Dipole", Lucas, P., Am.J. Phys., 54(7), pp. 666–667 (1986), the disclosure of which is hereby incorporated by reference herein. The coils, as well as frame 30, are constructed and arranged to permit insertion of a body part of a living patient into the sensing volume 32. Desirably, the frame has openings 40 coaxial with the various coils so that the patient's body may be inserted into the sensing volume 32 through one such opening 40 and so that the physician may gain access to the patient while the patient is within the sensing volume through the other openings. The frame may be constructed of essentially any rigid material. Dielectric materials are preferred because they do not create eddy currents when magnetic fields are changed. The frame may include quick-release or breakable connections between the various coils and frame elements. This allows the physician to move the coils and frame away from the patient immediately in the event of an emergency requiring totally unimpeded access to the patient.

All of the coils are connected to a coil driver 42, which in turn is connected via an output interface 44 to receive output from a computer 46. Computer 46 may be a digital computer of the type commonly referred to as a workstation or dedicated computer. Output interface 44 is arranged to accept the commands from the computer and actuate coil driver 42 in response to such commands. Coil driver 42 includes a conventional DC power supply 47 and conventional switching devices schematically indicated at 48 for connecting the coils of each pair to the power supply 47 either in a forward configuration or in a reverse configuration as commanded by computer 46 through interface 44. In the forward configuration, the coils are connected in a series-aiding arrangement such that current passing through both coils of the pair flows in the same direction about the pair axis. For example, when the coils 34 of the X-axis coil set are in the forward or series aiding configuration, they are connected in series so that current passing through both coils will flow counterclockwise around the X axes as seen from the positive-X end thereof. When the two coils of a pair are in the reverse configuration, they are connected in series opposition so that a current will pass through both coils in series, but will flow in opposite directions around the axis in the two coils of the pair. Current will flow clockwise around the X axis in one coil 34 but counterclockwise around the X axis in the other coil 34.

The apparatus further includes a patient monitoring probe 50. Monitoring probe 50 includes an elongated body 52 having a proximal end 54 and a distal end 56 adapted for insertion into the body of the patient. In the particular embodiment illustrated, the probe body 52 is an elongated, flexible shaft adopted to fit inside a conventional endoscope 53, which in turn may be introduced into the body. Endoscope 53 has one or more bores or passageways for conducting surgical instruments, fluids and the like so as to introduce the same into the patient's body, and probe body 52 may fit within one such bore. Such bores or passageways may also be used for passage of endoscopic surgical instruments or other treatment devices or substances. Alternatively or additionally, probe body 52 or the endoscope 53 may include known electrical, optical or electro-optical devices for providing a local image of the tissues surrounding distal end 56 such as video cameras and fiber-optic bundles. The endoscope may be connected to conventional medical treatment apparatus 58 for introducing and/or withdrawing fluids, for observing the tissues surrounding the tip by means of the electrical or electro-optical devices and for performing other conventional medical treatment applications commonly performed through probes inserted into the body.

A sensor 60 is mounted to the probe body 52 adjacent the distal end 56. As best seen in FIG. 2, sensor 60 includes a plurality of planar sensing elements 62, 64 and 66. Element 62 is arranged normal to a common sensor axis X'. Thus, the vector X' illustrated in FIG. 2 extending on the X' axiss of the sensor is normal to planar sensing element 62. Likewise, element 64 is normal to the Y' direction of the sensor and element 66 isnormal to the Z' direction The directions X', Y' and Z' are orthogonal to one another, and hence the planes of elements 62, 64 and 66 are perpendicular to one another as well. Each sensing element incorporates material providing a Hall effect so that the sensing element provides an output voltage proportional to the component of the magnetic field in the vicinity of the sensor normal to the face of the particular sensing element. Thus, sensing element 62 incorporates a thin film of galvanomagnetic material such as indium arsenide, gallium arsenide or others, on its surface, a pair of excitation leads 68 connected to two opposite edges of the film and a pair of output voltage leads 70 connected to the remaining edges. In operation, when a current is passed between edges 68 and a magnetic field is present in the vicinity of the sensor, a voltage appears between leads 70 proportional to the component of the field perpendicular to the sensor surface. Stated another way, where B is the local magnetic field vector and X' is the vector in the X' along the axis of the sensor perpendicular to elements 62, the output voltage $V_{062}$ from element 62 is:

$$V_{062} = K(B \cdot X') + V_{I62}.$$

Where the $V_{062}$ is the output voltage, K is a proportionality factor and $V_{I62}$ is the output voltage from element 62 at zero applied magnetic field. Element 64 has similar leads (not shown) and similarly produces an output voltage:

$$V_{064} = K(B \cdot Y') + V_{I64}$$

Where $V_{064}$ is the output voltage from element 64; Y' is the unit vector in the Y' direction; and $V_{I64}$ is the output voltage from element 64 at zero applied magnetic field. Likewise, element 66 produces output voltage $V_{066}$:

$$V_{066} = K(B \cdot Z') + V_{I66}$$

Where Z' is the unit vector in the Z' direction and $V_{I66}$ is the output voltage from element 66 at zero applied magnetic field. Because the sensor is disposed in the distal tip 56 of probe body 52, the position and orientation of sensor 60 are not fixed with respect to the X, Y and Z reference directions of frame structure 30 and coils 34–38. Thus, the local axes X', Y' and Z' of sensor 60 can be at any orientation with respect to the axes X, Y and Z of the coils and frame structure.

The leads of sensor 60, including leads 68 and 70 and other leads associated with other sensing elements (not shown) are connected to a drive and amplification unit 72 (FIG. 1) via cable 74 extending through the body 52 of the probe. Drive and amplification unit 72 is arranged to apply the appropriate excitation voltages to the elements of sensor 60 and to amplify the output voltages $V_{066}$, $V_{064}$, $V_{062}$ of the various sensing elements. The drive and amplification unit 72 is connected to an analog to digital converter 74, which in turn is connected to an input of computer 46. Although only a single connection is shown, it should be appreciated that converter 74 is a multi-channel device, with multiple connections and/or with multiplexing arrangements for delivering digital representations of all of the output signals from all of the sensing elements in sensor 60 to computer 46.

The apparatus further includes a fiducial marker 76 (FIG. 1) which incorporates a sensor 80 and a marker body 78.

Marker body 78 is arranged for mounting to a biddy part of the patient in a substantially fixed position relative to such body part. Thus, the marker body 78 may incorporate clamps, bands, rings or straps for fastening it onto the exterior of a patient's head, limb or torso. Alternatively or additionally, body 78 may include apertures or notches to accommodate sutures, pins, surgical staples or other fastening devices. The body of the fiducial marker may also be fastened to the patient's body with conventional surgical adhesive tape, bandages or the like. At least one part of the fiducial marker, such as the marker body 78, the sensor 80 or both is formed from a material which is detectable in a patient imaging technique such as X-ray, magnetic resonance imaging ("MRI"), computerized axial tomography ("CAT"), or other commonly utilized imaging modalities. Sensor 80 of the fiducial marker is substantially the same as the sensor 60 of the monitoring probe 50. Sensor 80 is connected to a drive and amplification unit 82, which in turn is connected through an analog to digital converter 84 to computer 46. Unit 82 and converter 84 are similar to drive and amplification unit 72 and analog to digital converter 74.

The apparatus further includes an image storage unit 86 for storing an image of a patient, or of a body part of a patient, in digital form. Typically, image storage unit 86 includes conventional computer memory devices. An image input device 88 is also provided. Input device 88 may include conventional digital data input devices such as disk drives, data communication links or the like for accepting images in digital form from any suitable imaging equipment such as x-ray equipment, MRI, CAT or video equipment, and for transferring the input images into image storage device 86. A display monitor 90 is linked to computer 46. Display monitor 90 is equipped with manual input devices such as knobs 92, 94 and 96, and linked to computer 46 so that the settings of these knobs can be communicated to the computer. The data input devices may also include a mouse, trackball, joystick or keyboard.

In a method according to one embodiment of the invention, a body part of the patient, such as the head, is imaged using conventional imaging apparatus such as MRI, CAT, X-ray or the like, while the fiducial marker 76 is mounted on the body part. Thus, the image data so acquired includes a depiction of the fiducial marker. In this regard, it is not essential that the entire fiducial marker be mounted on the patient's body part at this stage of the process. Thus, if the magnetic sensor 80 is detachable from marker body 78, and if marker body 78 can be visualized by the imaging modality employed, then the sensor 80 may be disconnected from the marker body during this stage of the process. Also, the sensor of the fiducial marker may be disconnected from the remainder of the apparatus during this stage of the process. In this stage of the process, the patient need not be, and typically is not, positioned in frame 30 or in the imaging volume 32. Typically, the patient is imaged in an entirely separate room or facility. After this imaging step, the fiducial marker remains in place on the patient throughout the remainder of the process. The image data depicting the patient's body part, including the depiction of fiducial marker 76, is transferred through input device 88 to image storage unit 86. The image data may include an image in a single plane or, more desirably, images in plural planes or a fully three-dimensional image, such as a map of radioopacity or magnetic resonance activity over a full three-dimensional volume incorporating a portion of the body part. The image data may be stored as output data wherein individual data elements represent densities or colors to be displayed on a pictorial representation of the image. Alternatively, the image may be stored in the form of input data such as time domain or frequency domain representations of magnetic resonance signals, or unprocessed tomographic data, from which a pictorial representation can be reconstructed.

In the next stage of the method, the body part of the patient is positioned within sensing volume 32. Probe 50 is advanced into the patient's body using conventional techniques of the medical arts. Computer 46 actuates coil driver 48 to operate the coils in a predetermined, repetitive sequence. The sequence includes a null state, in which all of the coils are turned off and the only magnetic fields in sensing volume 32 are those introduced by extraneous sources, such as the earth's magnetic field, stray magnetic fields from nearby items and the like. Also, the sequence includes a forward or homogeneous-field stage for each set of coils. When each set of coils is being driven in its forward stage, in the aforementioned series-aiding configuration with codirectional current flow in both coils, such set provides a substantially homogeneous unidirectional magnetic field oriented along its axis. For example, the X-direction coils 34 in the forward state provides a field consisting essentially of flux directed parallel to the X-axis, of substantially equal magnitude throughout a central region of sensing volume 32, adjacent the midpoint of the sensing volume, i.e., the origin or intersection 39 of the X, Y and Z axes. Typically, the field is homogeneous to within about 1% over a region extending from the origin and encompassing about 62% of the distance between the coils, and extending laterally outwardly from the axes for a distance equal to about 25% of the coil diameter. The three coil sets are actuated separately, at different times during the sequence, so that only one coil set is active in the forward mode at any given time.

The sequence also includes gradient or reverse configuration mode actuation of each coil set. In the reverse or gradient mode, with the currents flowing counterdirectionally in the two coils of each set, the field generated by each coil set incorporates a component directed along the axis between the coils and having a substantially linear, uniform gradient along that axis. For example, when the X-direction coils 34 are actuated in the gradient mode, the field has the configuration illustrated in FIGS. 3, 4 and 5. In FIG. 3, $R_x$ is the component of the reverse or gradient field in the X-direction, i.e., parallel to the X-axis. As seen in FIG. 3, this component has a low negative value at one end of the sensing volume. The X-directed component $R_x$ increases monotonically and linearly with increasing values of X, passing through 0 at approximately X=0, i.e, at the origin 39. The value or magnitude of the X-directed component at any given location along the X-axes is the same for any Y and Z. $R_x$, thus is a function only of X, and is constant with respect to Y and Z.

The reverse or gradient field generated by X-axis coils 34 also includes a radial component perpendicular to the X axis. The radial component is symmetrical about the X-axis and is directed away from the X axis. The radial component resolves into a Y-directed component and a Z-directed component. As seen in FIG. 4, the Y-directed component $R_y$ of (the reverse or gradient field generated by the X-coils 34 varies monotonically with Y, reaching 0 at Y=0, i.e., at the X - Z plane. The Z-direction component Rz of the X-coil reverse or gradient field has a similar configuration (FIG. 5). Thus, $R_z$ is proportional to Z. The proportionality constant or slope of $R_y$ versus Y is about one third of the proportionality constant for $R_x$ versus X. Likewise, the proportionality constant or slope for $R_z$ versus Z is also about one third of the proportionality constant for $R_x$ versus X.

The foregoing discussion with respect to FIGS. 3, 4 and 5 refers to the various components of a single reverse or gradient field, generated by X-axis coils 34. The reverse or gradient fields generated by the Y-axis coils 36 and by the Z-axes coils 38 have the same configurations, but along different axes. Thus, the reversed or gradient field generated by Y-axis coils 36 has a component $R_y$ which increases monotonically with increasing values of Y (with increasing displacement along the Y-axis in the +Y direction) but which it does not substantially vary with X or Z at any given value of Y. This component also has a value of about 0 at the Y=0 point, i.e., at the origin 39 and along the X-Z plane. The same Y-axis gradient field has a redial component perpendicular to the Y axis. The redial component resolves to a component in the X-direction which is proportional to X and a component in the Z-direction proportional to Z. The proportionality constants of the X and Z components with X and Z distance, respectively, about one third the proportionality constant of the Y component with Y distance.

Likewise, the reverse or gradient field provided by Z-axis coils 38 has a Z-direction component varying monotonically with Z and reaching about 0 at the origin (Z=0), this component being constant with respect to X and Y within the central region of the sensing volume 32. The reverse or gradient field generated by coils 38 includes an X-direction component proportional to X and a Y-directed component proportional to Y both of these proportionality constants being less than the proportionality constant of the Z-direction component.

With the reverse or gradient fields as well, the individual coil sets are actuated separately, at different times from one another, so that only one coil set is actuated at any given time, and so that none of the coil sets is actuated for gradient-field mode while another set is in homogeneous-field mode. The various actuations are repeated cyclically. The particular sequence within each cycle is unimportant. Thus, each cycle may include actuation of each coil set to produce its respective uniform field, followed by actuation of each coil set to produce its reversed or gradient field followed by deactivation of all coil sets. Alternatively, the sequence may include actuation of the X-direction coil said to produce its uniform field, then to produce its reversed or gradient field, followed by similar actuation of the Y and Z coil sets and deactivation of all coil sets, or any combination of these patterns. However, computer 46 maintains a record of the coil actuation for each moment in the sequence, so that incoming data from sensors 60 and 80 can be associated with particular coil set activations. The full sequence is repeated rapidly so that each sequence takes about 10 to about 100 milliseconds.

As the fields are switched on and off in the sequence, computer 46 controls acquisition of data from sensors 60 and 80 so that signals representing each field are acquired at a preselected acquisition time during each switching cycle. Thus, as each coil pair is switched on in a particular mode, the magnitude of the field generated by that coil pair rises exponentially to a constant value according to the equation $$M_t = M_c(1-e^{(-t/tau)})$$

where:

t is time;

$M_t$ is the instantaneous field magnitude at time t;

$M_c$ is the constant or steady-state magnitude; and tau is a time constant proportional to the inductance of the coil set and inversely proportional to the series resistance.

Because the acquisition time is the same for all switching cycles, the instantaneous field magnitude $M_t$ at the acquisition time is always a constant proportion of the steady-state field magnitude $M_c$. For example, the delay between the start of a switching cycle and the acquisition time may be about equal to one times the time constant tau, i.e., about 20 percent of the delay time which would be required to reach a substantially steady-state condition. In this arrangement, the instantaneous field magnitude at the acquisition time in each cycle is about 63 percent of the steady-state value. Because each switching cycle can be terminated, and a new switching cycle begun, immediately after the acquisition time, this arrangement allows many more measurements per unit time than the alternative arrangement in which each coil pair is allowed to come to steady state before data acquisition. In a variant of this scheme, the acquisition time can be controlled by monitoring the instantaneous current through the coil sets. The system may be arranged to acquire data from sensors 60 and 80 on each cycle when the instantaneous current in the particular coil set being activated rises to a preselected trigger value, preferably less than the equilibrium current. In this arrangement as well, the sensor data samples will be taken at a consistent field magnitude from cycle to cycle. While the coils are repeatedly activated, signals are obtained from sensors 60 and 80, amplified, digitized and fed to computer 46. The signals are used to ascertain the orientation and position of the sensor, and the attached probe, within the sensing volume 32, in the X, Y and Z coordinate system. At each stage of each cycle, the computer acquires data representing the component of the field in the X', Y' and Z' directions of sensor 60, so that there is a separate data entry for the field in each such local direction during each coil actuation. Each data entry is corrected by subtracting the corresponding data entry for the coils-off of null-field condition in the same cycle. For example, all of the readings for elements 62 giving the field in the X' direction are corrected by subtracting the value for the field component in the X' direction acquired during the null-field condition. This removes any effect of fields other than those applied by the coils. References hereinbelow to "null-corrected" values of sensor readings should be understood as referring to the values corrected in this manner. The null-corrected values for the sensor readings acquired during generation of homogeneous fields are referred to as "$H_{m,n}$" where m is an letter indicating which sensing element acquired the value and n is a letter indicating which coil pair generated the homogeneous field during acquisition of the values. The notation is indicated in table I, below:

TABLE I

SENSING ELEMENT READINGS FOR HOMOGENEOUS FIELDS

| SENSING ELEMENT | X Coil Pair | Y Coil Pair | Z Coil Pair |
|---|---|---|---|
| X'-62 | $H_{x',x}$ | $H_{x',y}$ | $H_{x',z}$ |
| Y'-64 | $H_{y',x}$ | $H_{y',y}$ | $H_{y',z}$ |
| Z'-66 | $H_{z',x}$ | $H_{z',y}$ | $H_{z',z}$ |

The values acquired during all of the homogeneous-fields thus form a 3×3 matrix. These values are normalized by dividing each such value by the magnitude of the flux generated by the particular pair, i.e., by the magnitude of the total flux vector applied by the coil pair. That magnitude in turn is the square root of the sum of the squares of the individual sensor readings:

$$Hx = sqrt[(H_{x',x})^2 + (H_{y',x})^2 + (H_{z',x})^2]$$

$$Hy = sqrt[(H_{x',y})^2 + (H_{y',y})^2 + (H_{z',y})^2]$$

$$Hz=sqrt[(H_{x',z})^2 +(H_{y',z})^2+(H_{z',z})^2]$$

Where $H_x$ is the magnitude of the magnetic flux applied by the X-axis coil set 34 during uniform field activation and $Hy_2$ and $H_{z3}$ are similar magnitudes for the flux applied by the Y-axis set 36 and by the Z-axis set 38 respectively. The term "sqrt" means "square root of" the expression in brackets; ^2 means the square of the preceding expression. These magnitudes are then used to compute normalized values. That is, each sensor reading taken during a given homogeneous-field actuation is divided by the magnitude of the flux generated during that actuation:

$$H'_{x',x}=H_{x',x}/Hx \quad H'_{x',y}=H_{x',y}/Hy \quad H'_{x',z}=H_{x',z}/Hz$$
$$H'_{y',x}=H_{y',x}/Hx \quad H'_{y',y}=H_{y',y}/Hy \quad H'_{y',z}=H_{y',z}/Hz$$
$$H'_{z',x}=H_{z',x}/Hx \quad H'_{z',y}=Hz',y/Hy \quad H'_{z',z}=H_{z',z}/Hz$$

The orientation of the sensor—the angles of the sensor X', Y' and Z' axes with respect to the X, Y and Z axes of the frame 30 and coil sets can be determined directly from the normalized values. Less than all of the values are needed for calculation of the orientation from all of the homogeneous fields. The system selects a set of values having the highest magnitude, and hence the greatest signal to noise ratio, for use in the calculation.

The orientation of the sensor with respect to the X,Y,Z coordinate system of the coils can be expressed in many ways. Preferably, however, the orientation is expressed as three angles referred to a pitch, roll and yaw. All of these are referenced to an assumed "home" or zero position in which the X', Y', Z' local directions of the sensor are aligned with the X,Y,Z reference directions of the coil system. Pitch is the angle 93 (FIG. 2) between the Z' local direction of the sensor and the Z reference direction. It can be calculated as:

$$Pitch=arccos(H'_{z',z})$$

Yaw is the angle 94 between the projection of the sensor Z' axis onto the X-Y plane and the Y reference direction. It is calculable as:

$$Yaw=arctan(H'_{z',x}/H'_{z',y})$$

In this notation, yaw is undefined for a zero-pitch condition. Roll is defined as the angle 95 between the local direction X' of the sensor and the system reference Z direction. It can be calculated as:

$$Roll=arctan(H'_{y',z}/H'_{x',z})$$

Any other internally consistent set of angles can be used to specify orientation. Moreover, orientation of the sensor can be fully specified by specifying any two unit vectors of the sensor local coordinate system in terms of the X,Y,Z reference coordinate system. Merely by way of example:

$$X'=i(H_{x',x})+j(H'_{x',y})+k(H'_{x',z})$$

where

X' is the unit vector in the X' direction; and i,j,k are the unit vectors in the X,Y,Z reference directions.

The system also acquires data representing the sensor readings acquired during application of the gradient fields. As with the data acquired during generation of the homogeneous fields, above, the gradient field data is corrected by subtracting the null-field values for each sensor. The corrected values are then taken as data representing sensor readings, and hence, field components in particular X' Y' and Z' directions during application of the gradient fields by the different coil sets. Thus, as indicated in Table II, below, $R_{x',x}$ represents the X' sensor reading, and hence the field component in the X' local direction of sensor 60 while the X-axis coils are operating in the reversed or gradient field mode, $R_{x',y}$ represents the similar component in the X' local direction during gradient field operation of the Y-axis coil pair and so on:

TABLE II

| | SENSING ELEMENT READINGS FOR GRADIENT FIELDS | | |
|---|---|---|---|
| SENSING ELEMENT | X Coil Pair | Y Coil Pair | Z Coil Pair |
| X'-62 | Rx',x | Rx',y | Rx',z |
| Y'-64 | Ry',x | Ry',y | Ry',z |
| Z'-66 | Rz',x | Rz',z | Rz',z |

The magnitude of the total flux vectors at sensor 60 during actuation of each coil set in a gradient mode are calculated by computer 46:

$$|Bx|=sqrt[(R_{x',x})^2+(R_{y',x})^2+(R_{z',x})^2]$$
$$|By|=sqrt[(R_{x',y})^2+(R_{y',y})^2+(R_{z',y})^2]$$
$$|Bz|=sqrt[(R_{x',z})^2+(R_{y',z})^2+(R_{z',z})^2]$$

Where |Bx| is the magnitude of the flux at the sensor during operation of the X-axis coil set 34 in a gradient or reversed mode, and where |By| is the magnitude of the flux vector at sensor 60 during gradient field operation of the Y-direction coil set 36 and where |Bz| is the magnitude of the flux vector at the sensor during operation of the Z-axis coil set 38.

Although the magnitude of the total flux vectors for each gradient field can be readily calculated as described above from the gradient field sensor readings $R_{x',x} \ldots R_{z',z}$, the direction of the gradient fields flux vector in the XYZ reference coordinate system defined by the coils is not ascertainable from these values alone. Thus, the $R_{x',x} \ldots R_{z',z}$ values represent components in the X', Y' and Z' local directions of the sensor. The normalized homogeneous-field values $H'_{11} \ldots H'_{33}$ are used in conjunction with the gradient field component values for each coil set to derive a projection of the total gradient field vector for each coil set onto the axis of that coil set, and thus derive the component of the gradient field vector on the axis of the coil set which was activated to produce that gradient field.

First, the system computes the magnitude of a difference vector between the total gradient field vector and the normalized unit magnitude homogeneous-field vector generated by the same coil pair. For example, as shown in FIG. 6, the system computes the magnitude of the difference vector $d_x$ representing the vector difference between the total flux $B_x$ during operation of the X-axis coil set in gradient mode and the normalized, unit length vector, $H'_x$ representing a unit vector in the direction of the flux during operation of the X-axis coil set in the homogeneous-field mode. That latter direction of course is along the X-axis of the coil sets. The components of the difference vector in the X', Y', Z' local coordinate system of the sensor are calculable directly from the gradient field sensor values $R_{x',x}$, $R_{y',x}$, $R_{z',x}$ acquired during operation of the X coil set in gradient mode and from the normalized homogeneousfield sensor values $H'_{x',x}$, $H'_{y',x}$, $H'_{z',x}$ acquired during operation of the same coil set in homogeneous-field mode. Thus:

$$|dx|=sqrt[(R_{x',x}-H'_{x',x})^2+(R_{y',x}-H'_{y',x})^2+(R_{z',x}-H'_{z',x})^2]$$

Where |dX| is the magnitude of the difference vector. Inasmuch as the magnitudes of the unit vector $H'_x$, of the gradient field total flux vector $B_x$ and of the difference vector dX are all known, the angles between these vectors can be calculated by application of the law of cosines. In particular, the angle $T_x$ between the total gradient field vector $B_x$ at the sensor during operation of the X-direction coil set in gradient mode and the unit vector $H'_x$ can be calculated as:

$$Tx = arccos[(1+|Bx|^2-|dX|^2)/(2*|Bx|)]$$

Because the homogeneous field generated by the X-axis coil set has flux directed along the X-axis, angle $T_x$ represents the angle between the gradient field total flux vector $B_x$ and the X-axis. The component of the gradient field total flux vector $B_x$ in the direction of the X-axis reference direction is simply:

$$R_x = (|B_x|)\cos(T_x)$$

This represents the component of flux in the X-direction at sensor 60 during operation of the X-axis coil set 34 in the gradient or reverse field mode. As noted above, the component of flux during this operation of the X-direction coil set is substantially proportional to position in the X-direction (FIG. 3). Thus:

$$X\ Position\ (mm) = (M_x)\ (R_x)$$

Where $M_x$ is a conversion factor. The conversion factor represents the slope of the function relating the X component of flux $R_x$ to distance in the X direction. $M_x$ may also be scaled to take account of the sensitivity of the various elements in the sensor and the gains of the various amplification channels, assuming all of these are equal for all of the sensors. Alternatively, additional sensitivity scaling factors may be applied to convert the voltages $V_{062}$, $V_{064}$, $V_{066}$ derived from each sensing element into actual numerical values of the magnetic flux components, so that separate scaling factors are applied to the readings from the different sensing elements.

The difference vectors and angles are computed in the exactly analogous way to derive the Y-axis component $R_y$ of the flux vector $B_y$ detected at sensor 60 during operation of the Y-direction coil set in the gradient mode and to derive the Z-axis component Rz in the z direction during gradient operation of the Z-axis coils. The magnitudes of the difference vectors are calculated as:

$$|dy| = sqrt[(R_{x',y}-H'_{x',y})^2 + (R_{y',y}-H'_{y',y})^2 + (R_{z',y}-H'_{z',y})^2]$$

and $$|dz| = sqrt[(R_{x',z}-H'_{x',z})^2 + (R_{y',z}-H'_{y',z})^2 + (R_{z',z}-H'_{z',z})^2]$$

Where |dY| and |dZ| are the magnitudes of the difference vectors associated with the Y-axis and Z-axis coils, in the same way as |dX| is calculated above. Angles Ty and Tz are calculated in the same manner as Tx, using the law of cosines:

$$Ty = arccos[(1+|By|^2-|dY|^2)/(2*|By|)]$$

and $$Tz = arccos[(1+|Bz|^2-|dZ|^2)/(2|Bz|)]$$

Y-direction and Z-direction positions are calculated from these components and angles in exactly the same way as X-direction positions. Thus:

$$Ry = (|By|)\cos\ Ty$$

$$Rz = (|Bz|)\cos\ Tz$$

$$Y\ Position = (My)(Ry)$$

$$Z\ Position = (Mz)(Rz)$$

Thus, each time the coils cycle through the null, homogeneous and gradient field states, computer 46 recalculates the position and orientation of sensor 60. Inasmuch as sensor 60 is attached to the distal tip 56 of probe body 52, these calculations yield the position and orientation of the probe body distal tip.

In foregoing discussion, the conversion factor $M_x$ relating X-direction position to the magnitude of the X-direction component $R_x$ is assumed to be exactly constant and exactly uniform for all values of Y and Z. Likewise, the corresponding conversion factors relating Y-direction position to magnitude of the Y-direction flux component and relating Z-direction position to magnitude of the Z-direction flux component are assumed constant. The accuracy of the position determination can be enhanced by calibrating the instrument to derive a map of actual conversion factors for various positions in the sensing volume. In the calibration step, the actual magnitude of the field component in each axial direction is measured at various known values of X, Y and Z during reverse or gradient-field operation of the coil set associated with that axis. For example, the Y-direction component is measured at known locations during gradient-field operation of the Y-axis coil set. Each gradient field is substantially symmetrical about the axis of the associated coil set. Therefore, the calibrating measurements can be taken at points on a single plane including the axis of the coil set, and the same values can be assumed to apply to the points corresponding to rotation of the actually-measured points about the axis of the coil set. The measured magnitudes are used to derive actual conversion factors applicable at each of the known positions. The same data is used to derive average conversion factors for each direction, applicable to the sensing volume as a whole, as by finding the single factor for a given direction which best fits all of the data acquired in calibration.

In operation, the X, Y and Z coordinates of the sensor are determined as a first approximation using the average conversion factors and the measured values of gradient-field components $R_x$, $RY_y$ and $R_z$. These first-approximation coordinates are then used to determine actual conversion factors by interpolation between the actual conversion factors for the closest points where measurements were taken during the calibration step of the process. The resulting conversion factors are then applied with the measured values of the gradient-field components $R_x$, $RY_y$ and $R_z$ to determine second approximated coordinates, which are in turn used to determine new values for the actual conversion factors by interpolation in the calibration data. These steps are repeated until the approximation converges to constant values of the various coordinates, which represent the best approximation of position.

In exactly the same way, the computer acquires flux component values from the sensing elements of sensor 80 on fiducial marker 76. On each cycle of the coils, the computer drives the position and orientation of the fiducial marker as well.

Computer 46 takes the data defining the image of the patient's body part from storage device 86 and displays a pictorial representation of the image I on monitor 90.

Because the image of the patient's body part acquired during the previous imaging step includes a depiction of fiducial marker 76, the displayed image I will include a pictorial depiction 102 of the fiducial marker 76. The computer also actuates monitor 90 to display a pictorial representation 104 of fiducial marker 76 at a location on the monitor screen. Representation 104 is displayed at a position corresponding to its position in the XYZ frame of reference, i.e., to the position of the fiducial marker as derived from the magnetic field measurements. The orientation of representation 104 is set to correspond to the orientation of the fiducial marker determined from the magnetic field measurements. If the representations 104 of the fiducial marker is in registration with depiction 102 of the same marker on the monitor screen, this indicates that the image of the patient's body part is displayed at a location and orientation on the monitor screen corresponding to the location and orientation of the body part within the XYZ reference coordinate system.

At the start of the displaying step, the image I of the patient's body part is typically misregistered. Thus, the depiction 102 of the fiducial marker incorporated in the image is out of registration with the representation 104 of the fiducial marker derived from the magnetic positioning and orientation data. The user manually instructs the computer to reorient the image by applying appropriate inputs to manual input devices 92, 94 and 96 to shift and turn the image until the depiction 102 overlies the representation 104 and so that these two pictorial elements are properly aligned with one another. Where the stored image includes images or "slices" on a plurality of planes through the body part, the manual adjustments to the image may include selection of an image in the correct plane to show the depiction 102 of the fiducial sensor in a true size, with the imaging plane cutting through the sensor. By means of these manual control inputs, the user effectively inputs relationship data into the system informing the system of the relationship between the initial frame of reference of the image and the X-Y-Z frame of reference of the system, and the system transforms the image into an image in the X-Y-Z frame of reference.

Once the manual controls have been actuated to bring depiction 102 and representation 104 of the fiducial marker with one another, a further "lock" signal is sent to the computer through a conventional data input device such as a keyboard 106 indicating that such registration has been accomplished. After receipt of the "lock" signal the computer continually maintains registration of the fiducial marker depiction 102 in the image with the magnetic data-derived representation 104 of the fiducial marker. Thus, if the position and orientation data for fiducial marker 76 obtained through the magnetic field measurements indicate a change in the position, orientation or both of the fiducial marker 76, the computer will shift the magnetic field derived representation 104 of the fiducial marker on monitor 90 accordingly, and will also transform the image I, including the depiction 102 of the fiducial marker, in the same way. Thus;, there is no need for the patient to remain in a fixed position during the procedure.

For example, the particular image I shown in FIG. 1 is an image taken on a cutting plane parallel to the Y-Z axes. If the position and orientation data for the fiducial marker 76 derived from the magnetic field measurements indicates that the patient's body part has moved by in the +Y direction and has rotated clockwise around the +X axes since the image was initially brought into registration, then computer 46 will transform the image and actuate monitor 90 to show the image displaced and rotated in the corresponding directions on the monitor screen. Methods of transforming stored images to show displacements and rotations in two and three dimensions are well known in the art, and need not be described in detail here. However, such methods are commonly employed to show the image transformed in response to arbitrarily input displacements and positions. Here, the transformation techniques are applied in response to true displacements and rotations of the body part measured by the magnetic field monitoring system.

At this point, the image I of the patient's body part is displayed on the screen of monitor 90 in a position corresponding to its true position and orientation in the XYZ reference coordinates of the frame and coils. The computer actuates display 90 to show a representation 108 of at least the distal end 56 of the probe 50. The position and orientation of representation 108 correspond to the position and orientation of the distal tip 56 derived from magnetic field measurements by sensor 60. As both the representation 108 and the image I are displayed on monitor 90 in positions and orientations corresponding to the true position and orientation of the probe and of the patient's body part in the X, Y, Z reference direction coordinate system, the combined representation 108 and image I on the monitor screen accurately depict the position of the probe distal tip 56 relative to the patient's body part. Also, as the position and orientation of probe distal tip 56 changes, the computer will alter the position and orientation of the probe representation 108 on the monitor screen. The representation of the monitoring probe tip 56 and of fiducial marker 76 may be pictorial representations or else may be schematic representations such as lines, arrows or the like.

Thus, the system will continually show the true relationship between the probe tip and the patient's body part. In effect, the system provides a result similar to that which would be achieved by continually imaging the patient during the medical procedure, as by continually taking X-ray, CAT, or MRI images to show the probe tip. However, the magnetic field monitoring steps according to this embodiment of the invention do not interfere with the ongoing medical procedure. No ionizing radiation is employed. Moreover, the magnetic fields used are so small that they do not exert any significant, perceptible forces on magnetic materials in the sensing region. The system is also substantially insensitive to the presence of magnetic materials and/or stray electromagnetic fields in the sensing volume. The coils typically provide good access to the sensing volume for the position to reach the patient through the openings 40, so that the physician can conduct the required procedure. Further, the coils and the supporting structure can be removed immediately for even better access of an emergency crises during the procedure.

The ability of the present system to provide accurate positional information, and to superpose a representation of the probe on an image of the patient's body is useful in many medical procedures, but is especially valuable in procedures where an endoscopic instrument is to be used in the brain. Although endoscopic instruments typically are equipped with devices such as miniature video cameras, fiberoptics or the like which provide an image of the tissues immediately surrounding the distal tip of the endoscope, such images do not permit the physician to establish the location of the tip in the brain, simply because many regions of the brain present the same endoscopic appearance. Using methods as discussed above, the physician can monitor the location and orientation of the instrument by viewing the representation of the distal tip of the probe against an image of the brain. Thus, the endoscopic instrument equipped with the probe can be used to perform surgical operations or other treatments in the brain, as by positioning the endoscope using the probe, removing the probe from the bore of the endoscope body 53 and then passing conventional endoscopic surgical instruments through the bore of the endoscope. Alternatively, the endoscope may have two bores, or one large bore, so that instruments may be inserted while the probe remains in place. Also, the sensor 60 may be mounted at the distal tip of the endoscope itself, so that the endoscope body 53 serves as the probe body. The methods and apparatus discussed above can also be used in all other areas of the body as, for example, in the spinal column; heart; otolaryngological tract; urogenital tract and organs; abdomen; and lungs. Additional embodiments of the invention provide a frameless stereotactic system. In a conventional stereotactic system, a rigid probe is guided by a frame mounted outside of the patient's body and fixed to a body part, so that the tip of the probe can be positioned at a precise location within the body. Thus the frame may be fixed to the skull and the probe advanced along a preselected line set by the frame. Using systems as described above, no frame is necessary; the position of the probe relative to the patient is determined from the measured magnetic field components at the probe and at the fiducial marker on the patient. Where the probe is rigid, the magnetic sensor on the probe may be disposed at the proximal end of the probe, which remains outside of the patient's body during the procedure. In this case, the computer system is arranged to calculate the position of the probe tip from the position and orientation of the sensor.

In a further method according to the invention, a plurality of body parts such as the portions of a patient's limb 174 and 175 (FIG. 7) joined at a common joint 177 may be provided with probes 176A and 176B respectively. Each such probe is similar to the fiducial marker 76 discussed above with reference to FIG. 1. Probe 176A is fastened by a band 180 to limb 174 so that the probe is held in substantially fixed position relative to the bone 182 within limb portion 174. To assure even greater accuracy, the probe 176 may be fastened directly to the bone, as by surgically inserting the probe into the limb, or by connecting the probe to pins (not shown) extending through the soft tissues of the limb to the bone. Likewise, probe 176B is fastened to limb portion 175 so that the probe is held in fixed position relative to the bone 183. Here again, an image of the body parts is acquired, as by X-ray, CAT, MRI or other imaging modality. The image includes images of probes 176A and 176B, as well as images of bones 182 and 183, and may also include images of other body parts such as the surrounding soft tissues.

In the same way as discussed above with reference to FIGS. 1–6, the image is input and stored in an image storage unit associated with computer 46. The limb is then placed in the sensing volume 32 of the apparatus. Sensors incorporated in probes 176A and 176B are connected to the drive and amplification units 72 and 82 of the apparatus. The positions and orientations of these probes are acquired by the apparatus based upon magnetic field measurements in the same way as discussed above with reference to FIGS. 1–6. The positions and orientations of the two sensors are monitored simultaneously. As shown in FIG. 8, the images $I_{182}$ and $I_{183}$ showing the two bones 182 and 183 are displayed on the monitor screen 90 by the computer. The displayed images include a depiction 186A of probe 176A and a further depiction of 186B of probe 176B. In the same manner as described above, the computer also displays representations 188A and 188B of probes 176A and 176B at positions corresponding to the positions of the probes determined by the magnetic field measurements. Utilizing the manual input controls associated with the computer, the user actuates the computer to change the position of Image $I_{182}$ until the depiction 186A of probe 176A in the image overlies the magnetic-field based representation 188A and is aligned therewith, whereupon the user inputs a lock signal. The user separately manually adjusts the position of image I 183 until the depiction 186B of probe 176B is superposed on the representation 188B derived from the magnetic field data in the correct alignment therewith. At this point, the user inputs a further lock signal.

Once both images have been aligned and placed in registration with the magnetic field frame of reference in this matter, both body parts are in initial, reference positions. Any subsequent movement of either probe 176A or 176B detected by magnetic field measurements is taken as showing movement of the associated body part 174 or 175. Thus, when probe 176A moves to the moved position indicated in broken lines in FIG. 7 at 176A prime, the computer transforms the image $I_{182}$ of the associated bone 182 to the transformed image $I'_{182}$ (FIG. 8). The rotation and/or translation applied to image $I_{182}$ to form transformed image $I'_{182}$ correspond to the rotation and translation of the probe in going from its starting position 176A to its moved position 176A'.

The image of each body part is treated independently, in accordance with position and orientation data derived from the associated probe. The system shows the images of the body parts, in particular, of bones 182 and 183, in true relative position and orientation as the bones move relative to one another. In effect, the system provides the equivalent of a continuous imaging system, such as a fluoroscopic imaging system, without the disadvantages thereof. The same system can also show the orientation and position of one or more medical instruments, such as one or more probes equipped with sensors as discussed above with reference to probe 50 of FIG. 1. As the images of both body parts are shown in true position and orientation relative to one another and relative to the XYZ reference direction coordinate system of the frame and coils, and as the representation of the instrument is likewise shown in true position and orientation, the instrument is presented in proper position and orientation relative to both body parts.

In the illustration of FIG. 8, the images $I_{182}$ and $I_{183}$ are shown as including the depictions 186A and 186B of the probes. However, after the images have been brought into registration with the XYZ coordinate system by aligning the depictions of the probes with the magnetic field-based representations 188A and 188B, there is no need for further visible display of the probe depictions 186 or of the probe representations 188. At this stage, the display may depict only the area of interest, such as at joint 177.

In each of the systems discussed above, the image of the patient is brought into registration with the XYZ coordinate system by manual alignment of the magnetic field derived representation of the probe with or marker with a depiction of the probe or marker in the image itself. However, this step can be automated, as by using automatic pattern recognition equipment to detect a depiction of the fiducial marker or probe in the patient image. With such automation, it is unnecessary to display a visible depiction or representation of a fiducial marker or probe. In the system discussed above with reference to FIG. 1 only one fiducial marker is provided on the patient's body part. Registration of the image data with the coordinate system thus depends upon the positional and orientation data for this single marker. For greater accuracy and versatility, a plurality of fiducial markers, and preferably three fiducial markers are employed at spaced apart, non-colinear locations on the patient's body part.

Where a plurality of independently movable body parts are to be located, as in the embodiment of FIGS. 7–8, plural probes may be mounted to each.

Alternatively or additionally, the patient's body part may be registered with the XYZ reference coordinate system through means other than a fiducial marker. In the simplest arrangement, the patient's body part is fixed to frame 30 at a known location and orientation, and the image I of the body part is displayed on monitor 90 at a location corresponding to this known location. Alternatively, the position and orientation of the patient's body part, such as the head shown in FIG. 1 is determined by mechanical or other non-magnetic measuring devices and that data is used to determine the proper position and orientation of the image I on screen 90.

A sensor used in a further embodiment of the invention includes three field-sensing elements in the form of semiconductor chips 250. (FIG. 9) Each chip includes one or more elongated bars of magnetoresistive material 252. Each such chip is sensitive to magnetic field components in the direction of the bars. The sensor further includes a foldable, sheetlike support 254 including a dielectric layer and having conductors 256 on the dielectric layer. Support 254 desirably is formed from a polyimide material of the type commonly used for flexible, tapelike electronic circuitry. Support 254 is initially in a generally cruciform shape as seen in FIG. 9. The support includes a rectangular or square central panel 262, a tip panel 264 projecting from one edge of central panel 262, and a pair of side panels 266 and 268 projecting from opposite edges of the central panel. The support further includes an elongated strip 266 projecting from the edge of central panel 262 opposite from tip panel 264.

One chip 250 is mounted on central panel 262; another is mounted on tip panel 264 and the third chip 250 is mounted on side panel 266. The magnetoresistive bars 252 of the chip mounted on side panel 266 are parallel to the bars 252 of the chip mounted on tip panel 264, but both are orthogonal to the bars of the chip mounted on center panel 262. A temperature sensitive chip 258, which may incorporate one or more thermistors, thermoresistive elements or other temperature-sensitive devices, is mounted to the other side panel 268 of the support. An amplification chip 260 is mounted to the elongated strip 266 of the support adjacent its juncture with the central panel 262. The components can be mounted on the support using conventional semiconductor mounting and connecting techniques adapted to operate on planar circuit panels. After the components are mounted on the support, the support is folded over a core 270. Core 270 is substantially in the form of a rectangular solid or cube, and preferably is formed from a dielectric material. The central panel 262 is positioned on one face 272 of the support. The tip panel 264, side panels 266 and 268 and strip 266 are folded over the edges of the core so as to position these on faces of the core adjoining face 272. The panels and strips are secured in position on the core.

In this condition, the finished sensor has magnetoresistive sensing elements 250 on three orthogonal faces of the cube, and the bars of the three elements extend in three orthogonal directions. The entire sensor, including the magnetoresistive elements, the temperature sensor 258 and amplifier 260 desirably is less than about 5 mm, and more preferably less than about 1 mm in width and thickness.

The sensor according to this embodiment may be mounted in an elongated probe body 280 so that the sensing elements are disposed at or near the distal tip of the probe body, and so that the elongated strip 266 of the sensor, and the conductors 256 thereon, extend towards the proximal end of the probe body for connection to external conductors (not shown). The compact construction of the sensor permits use of a probe body having a very small diameter, desirably about 0.8 mm or less. A probe according to this embodiment can be used in methods as discussed above. In this sensor, each sensing element is sensitive to field components in one direction parallel to the face of the sensor, rather than normal to the face as in the sensors discussed above. Also, the built-in amplifier at the sensor enhances the signal-to-noise ratio. Otherwise, the probe is used in the same manner as discussed above.

In a method according to a further aspect of the invention, the probe of FIGS. 9 and 10 is employed to take physiologic temperature measurements within the patient's body. As discussed above, the probe is inserted into the patient's body, and the distal tip of the probe is moved over a range of positions within the body. As the probe is moved, the magnetic field monitoring system keeps track of the location of the distal tip within the XYZ reference direction coordinate system of the frame, so that each temperature measurement is associated with a position in that coordinate system. Thus, a map of temperature versus position is stored in the memory of computer 46. Preferably, such a map is displayed or stored in association with an image of the relevant body part of the patient. As discussed above, such an image is brought into registration with the reference direction coordinate system of the magnetic field apparatus through use of a fiducial marker or through other means. Thus, the temperatures measured by the probe can be mapped onto the features of the body part as, for example, by shading or coloring various portions of the image to correspond with different temperatures or by showing contour lines overlaid on the body image as illustrated in FIG. 11.

Probes and methods as described with reference to FIGS. 9–11 can be utilized for example by inserting the probes into the body through natural body orifices to probe cavities such as the intestinal tract, urinary tract, and respiratory tract and detect regions of locally elevated temperature. Such regions are often associated with pathological conditions such as malignant tumors. Further, once such a region has been located and precisely mapped, the physician can use the same or a different probe to examine the area visually and/or to perform biopsy, surgical, excision or other treatment.

The temperature sensitive element 258 may be replaced or supplemented by one or more elements sensitive to any other physiologic variables, such as pH, ionic concentration, or others. Also the element or elements sensitive to temperature or to other physiologic variables can be formed separately from the magnetic sensor.

As an alternative to display of the mapped physiologic data superposed on an image of the body part, the mapped data may be displayed alone in pictorial form or otherwise. For example, a pictorial representation showing a region of elevated temperature can show the size and shape of a tumor even without superposition. The maps of the physiologic data desirably are derived and displayed in real time, during the procedure, so that the displayed maps (with or without superposed body part images) can guide the physician in further mapping. Thus, the physician may first move the probe over a limited number of widely-spaced locations in the region of interest to derive a coarse map. This coarse map can be used to locate regions requiring fine examination by mapping of closely-spaced points.

In further variants of the apparatus and methods discussed above, the Z-axes coils, and the corresponding uniform and gradient fields are omitted. Thus, the system uses only two orthogonally directed uniform fields and gradient fields from only two coil sets. However, the system can still derive the position and orientation of the probes in three dimensions. Because the flux vectors for the uniform X, Y and Z fields are orthogonal to one another, the flux vector for any one uniform field can be calculated by calculating the cross-product of the other two. Stated another way, the components which a hypothetical third uniform field flux vector would have in the X', Y', Z' coordinate system of the sensor can be calculated from the actual components of the other two uniform-field flux vectors in the same coordinate system. Thus, the normalized components $H'_{m',n}$ of a hypothetical Z-direction uniform field flux vector can be calculated from the actual normalized components measured for the X-direction and Y-direction fields:

$$H'x',z=(H'y',x*H'z',y-H'y',y*Hz',x)$$

$$H'y',z=(H'z',x*Hx',y-H'z',y*H'x',x)$$

$$H'z',z=(H'x',x*Hy',y-H'x',y*H'y',x)$$

Thus, all of the components $H'_{m',n}$ can be acquired by operating only the X and Y coil sets in uniform-field mode.

In the methods discussed above using three actual coil sets, the system calculates the magnitude of the projection of the reverse-field or gradient flux vector for each coil set onto axis of that coil set. However, the measured values for the reverse-field flux vector from one coil set can be eliminated. To find position for the axis corresponding to the missing coil set, the system calculates a projection of one of the flux vectors from one of the two remaining coil sets onto the third axis, as well as onto the axis of the coil set itself. This can be accomplished computationally by simply copying the values for one coil pair (one column in Table II) into the values for the third coil pair. Thus, where the Z-direction coil is omitted, the system sets:

$$R_{x',z}=R_{x',y}$$

$$R_{y',z}=R_{y',y}$$

$$R_{z',z}=R_{z',y}$$

and otherwise performs the computation in the same manner as described above. However, because the Y-direction field has its principal component along the Y-axis, and only a radial component along the Z-axis, the magnitude $R_z$ of the Z-axis component at any given Z-direction distance from the origin will be about −0.36 times the magnitude $R_y$ of the Y-direction component at an equal Y-direction distance. Thus, the Z-direction gradient $dR_z/dZ$ is about −0.36 the Y-direction gradient $dR_y/dY$, and the conversion factor $M_z$ used to convert Z-axis flux component to Z-axis distance is adjusted accordingly. Where a calibration step as discussed above is employed, the Z-axis conversion factor will be measured during Y-axis coil set activation.

The system according to this variant needs only two orthogonal coil sets, and thus provides even better access to the patient for the physician.

In the apparatus and methods discussed above, the various coil sets are actuated alternately, so that only one coil set is operating at any given time. However, the predetermined time sequence of magnetic fields used in other embodiments of the invention may include two or more fields applied simultaneously. The simultaneously-applied fields desirably are varied at different frequencies. In this case, the signals from the sensors representing the magnetic fields will incorporate separate components varying at these different frequencies. Each such component represents the sensor reading for one field. These components can be segregated by conventional filtering techniques and then evaluated separately to provided separate readings for the separate fields. For example, the magnitude of the AC waveform at each frequency can be evaluated separately. In each of the variants discussed above, the magnetic fields are applied by coaxially positioned Helmholtz coils. However, other magnetic field generating devices, such as permanent magnets or other coil arrangements can be employed. Also, it is particularly desirable to use uniform fields and fields having a component varying linearly with distance (uniform gradient) as discussed above. However, other combinations of magnetic fields can be employed. The fields need not necessarily include uniform fields, but can instead include a plurality of different fields with different, known gradients, provided that it is possible to mathematically deconvolute position and orientation from the sensor readings acquired during the various fields Also, fields with non-uniform gradients, and with non-linear variation of one or more components with distance can be employed. Such fields are less preferred. Moreover, the magnitude of each field component which is measured in the present invention desirably is quasilinear s with distance in a direction within the sensing volume. As used in this disclosure, a component magnitude is "quasilinear" with distance in a particular direction if the magnitude can be described by a polynomial function of position in such direction of the form:

$$a_0q^0+a_1q^1+a_2q^2+a_3q^3\ldots a_nq^n$$

in which q is position and in which the constant (zero-power) term, the first-power term or the sum of these terms predominates over the other terms. Stated another way, when evaluated for any distance q within the sensing volume the sum $(a_0q^0+a_1q^1)$ should be at least twice the sum $(a_2q^2+a_3q^3+\ldots a_nq^n)$. Preferably, $(a_0q^0+a_1q^1)$ is at least 5 times, and more preferably at least 10 times the sum $(a_2q^2+a_3q^3 \ldots a_nq^n)$. In the most preferred arrangements discussed above, $a_0q^0$ predominates in the homogeneous fields, the other terms being as close to zero as is practicable, whereas in the gradient fields, $a_1q^1$ predominates, and all of the other terms are as close to zero as is practicable. If a particular field includes components which are not measured in determining position or orientation, those extraneous components need not be quasilinear.

As these and other variations and combinations of the features discussed above can be utilized without departing from the present invention as defined by the claims, the foregoing description of the preferred embodiments should be taken by way of illustration rather than by way of limitation of the present invitation.

What is claimed is:

1. Apparatus for determining position of an object comprising:

(a) magnet means for generating a plurality of different magnetic fields in a sensing volume, each said field having at least one component having a magnitude which is quasilinear with respect to distance in a reference direction within said sensing volume, said magnitude being non-zero in at least some locations within said sensing volume;

(b) control means for actuating said magnet means to generate said fields in a predetermined sequence;

(c) a sensor connected to the object and movable within said sensing volume, and adapted to detect magnetic field components in at least two different local directions relative to the sensor and provide separate data representing each said component; and (d) calculation means for determining the position of said sensor from said data representing said magnetic field components detected during generation of said fields.

2. Apparatus as claimed in claim 1 wherein said magnet means includes means for generating a first substantially uniform magnetic field in a first reference direction within said sensing volume and, a second substantially uniform magnetic field in a second reference direction different from said first direction within said sensing volume and first and second gradient fields within said sensing volume, each said gradient field having a predetermined pattern of variation within said sensing volume, said control means being operative to actuate said magnet means to generate said gradient fields in sequence with said uniform fields, said calculation means being operative to determine the position of said sensor in said first and second reference directions within said sensing volume from said magnetic field components detected during generation of said gradient fields and said uniform fields.

3. Apparatus as claimed in claim 2 wherein said magnet means includes means for generating a third substantially uniform field within said sensing volume in a third reference direction different from said first and second reference directions, and for generating a third gradient field having a predetermined pattern of variation within said sensing volume, said control means being operative to actuate said third magnet means to generate said third uniform and gradient fields in sequence with said first and second uniform and gradient fields, said sensor being operative to detect magnetic field components in three different local directions relative to said sensor, said calculation means being operative to determine the position of said sensor within said sensing volume in said three reference directions.

4. Apparatus as claimed in claim 1 or claim 2 or claim 3 wherein said sensor has maximum dimensions less than about 5 mm.

5. Apparatus as claimed in claim 4 wherein said maximum dimensions are less than about 1 mm.

6. Apparatus as claimed in claim 4 wherein said sensor is adapted for disposition within the body of a human patient.

7. Apparatus as claimed in claim 6 wherein said sensing volume has minimum dimensions of at least about 30 cm.

8. Apparatus as claimed in claim 4 wherein said sensor includes a sensing body having a plurality of faces oriented in different directions and magnetically-sensitive layers disposed on said faces.

9. Apparatus as claimed in claim 2 or claim 3 wherein said magnet means are adapted to generate said gradient fields so that each said gradient field includes a component having magnitude varying according to a substantially linear monotonic gradient in one said reference direction within said sensing volume.

10. Apparatus as claimed in claim 1 or claim 2 or claim 3 wherein said magnet means includes a plurality of pairs of coils, the coils of each pair being disposed on opposite sides of said sensing volume.

11. Apparatus as claimed in claim 10 wherein said coils of each said pair are Helmholtz coils disposed substantially coaxially with one another so that the axis of each said pair extends in one said reference direction.

12. Apparatus as claimed in claim 1 or claim 2 or claim 3 wherein said control means is operative to bring said magnet means to an off condition wherein said magnet means provides no field in said sensing volume, said calculation means including means for registering baseline values of magnetic field components in said local directions measured by said sensor while said magnet means is in said off condition and correcting components measured while said magnet means is in other conditions in accordance with said baseline values.

13. Apparatus as claimed in claim 1 or claim 2 or claim 3 wherein said calculation means includes means for determining the orientation of said sensor in said sensing volume based upon the magnetic field components detected by said sensor.

14. Apparatus for determining orientation and position comprising:

(a) a magnet structure including at least two pairs of Helmholtz coils, the coils of each said pair being substantially coaxial with one another and defining a pair axis, and being disposed on opposite sides of a sensing volume, the axes of said pairs being substantially orthogonal to one another;

(b) control means for selectively actuating each said pair of Helmholtz coils in a homogeneous field state with codirectional current flow in both coils of the pair to thereby generate a magnetic field directed parallel to the pair axis of substantially uniform strength within said sensing volume, said control means also being operative to actuate each said pair of Helmholtz coils in a gradient field state with counterdirectional current flow in the coils of the pair to thereby generate a magnetic field having a component directed parallel to the axis of the pair, such component having a substantially linear gradient of magnitude in said sensing volume, said control means being operative to actuate said magnet structure so that only one pair of coils is actuated to only one state at any time;

(c) a probe movable within said sensing volume, said probe having mounted thereon sensor means for measuring magnetic field components in at least two different local directions relative to the probe and providing separate data representing each said component, whereby said sensor means will measure homogeneous-field components in said local directions while coil pairs are in said homogeneous field states and said sensor means will measure gradient-field components in said local directions while said coil pairs are in said gradient-field states; and (d) calculation means for determining the orientation of said probe relative to said pair axes from said data representing homogeneous-field components and determining the position of said probe in said sensing volume from said data representing homogeneous-field components and said gradient-field components.

15. Apparatus as claimed in claim 14 wherein said magnet structure includes three pairs of said Helmholtz coils and wherein said sensor means includes means for measuring magnetic field components in three said local directions orthogonal to one another.

16. Apparatus as claimed in claim 14 wherein said probe is adapted for disposition within the body of a human patient.

17. Apparatus as claimed in claim 16 wherein said probe is an elongated, flexible element having a proximal end and a distal end and said sensor means is disposed adjacent said distal end.

18. Apparatus as claimed in claim 16 wherein said pairs of Helmholtz coils are spaced apart from one another by distances of at least about 30 cm.

19. A method of determining the position of an object within a sensing volume comprising the steps of:

(a) generating a plurality of different magnetic fields in said sensing volume in a predetermined sequence, each field having at least one component having a magnitude which is quasilinear with respect to distance in a reference direction within the sensing volume;

(b) during generation of said fields measuring magnetic-field components in at least two different local directions relative to a sensor connected to the object to thereby provide separate data representing each of said magnetic field components; and (c) determining the position of said sensor within said sensing volume from said data representing said measured field components.

20. A method as claimed in claim 19 wherein said step of generating fields includes the step of generating first and second substantially uniform magnetic fields in first and second reference directions within said sensing volume and generating first and second gradient fields within said sensing volume, each said gradient field having a predetermined pattern of variation in one said reference direction, within said sensing volume, said step of measuring magnetic field components including the step of measuring homogeneous-field components during application of said uniform fields and measuring gradient-field components in said local directions at said sensor during generation of said gradient fields, and said determining step including the step of calculating the position of said sensor in said reference directions within said sensing volume from said measured homogeneous-field and gradient-field components.

21. A method as claimed in claim 20 further comprising the steps of generating a third substantially uniform field within said sensing volume in a third reference direction different from said first and second reference directions, and generating a third gradient field having a predetermined pattern of variation in said third reference direction within said sensing volume, said step of measuring said homogeneous-field components including the steps of measuring homogeneous-field components in three different local directions relative to said sensor during generation of said first, second and third uniform fields, said step of measuring said gradient-field components including the step of measuring gradient-field components in said three local directions during generation of said first, second and third gradient fields.

22. A method of displaying the location of a probe in a living subject comprising the steps of:

(a) providing at least one fiducial marker in fixed position relative to the subject;

(b) acquiring an image of the subject including a depiction of said at least one fiducial marker;

(c) determining the locations of said at least one fiducial marker and of said probe in a common frame of reference by measuring magnetic fields transmitted to or from said probe and said fiducial marker, whereby a position of said probe relative to said at least one fiducial marker is known; and (d) superposing a representation of said probe on said image of said subject at a position relative to said depiction of said at least one fiducial marker corresponding to the position of said probe relative to said at least one fiducial marker in said common frame of reference.

23. A method as claimed in claim 22 further comprising the steps of determining an orientation of said probe and of said at least one fiducial marker in said common frame of reference, said step of superposing said representation of said probe on said image of said subject being performed so that the orientation of said probe representation relative to the depiction of said at least one fiducial marker corresponds to the orientation of said probe relative to said at least one fiducial marker in said common frame of reference.

24. A method as claimed in claim 22 wherein said superposing step includes the step of displaying said representation of said probe in a display frame of reference so that the position of said probe representation corresponds to the position of said probe in said common frame of reference and displaying said image of said subject in said display frame of reference so that the location of said representation of each fiducial marker in said display frame of reference corresponds to the location of such fiducial marker in said common frame of reference.

25. A method of depicting a body part comprising the steps of:

(a) providing a sensor in fixed position relative to the body part and determining an orientation of said sensor in a fixed frame of reference;

(b) acquiring an image of the body part in a starting orientation;

(c) monitoring the orientation of said sensor in said frame of reference by measuring individual components of magnetic fields transmitted to or from said sensor, to thereby determine a moved orientation of said body part after movement of the body part from said starting orientation;

(d) transforming said image of said body part in said starting orientation into an image of said body part in said moved orientation and (e) displaying the transformed image.

26. A method as claimed in claim 25 wherein said monitoring, transforming and displaying steps are repeated as said body part is moved through a range of moved orientations so that a transformed image corresponding to said each said moved orientation is displayed substantially in real time while the body part is in such moved orientation.

27. A method as claimed in claim 25 wherein said monitoring, transforming and displaying steps are performed during a medical treatment procedure and said displaying step is performed so that the displayed image is visible to the physician performing such procedure, whereby such physician may view a transformed image corresponding to the current actual orientation of the body part at any time during the procedure.

28. A method as claimed in claim 26 or claim 27 wherein said step of providing a sensor includes the step of providing a separate sensor fixed to each of a plurality of body parts, said steps of acquiring an image and determining the orientation of the sensor including the steps of acquiring images of all of said body parts and determining the orientations of all of said sensors while said body parts are in respective starting positions, said step of monitoring the orientation of said sensor and determining moved orientation of the body part including the step of monitoring the orientation of all of said sensors and determining a separate moved orientation for each of said body parts, said transforming step including the step of transforming the image of each said body part into an image of that body part in its moved orientation, said displaying step including the step of displaying all of said transformed images together so that the orientations of said transformed images relative to one another correspond to the orientations of said body parts relative to one another.

29. A method as claimed in claim 28 further comprising the step of determining the position of said sensors in said fixed frame of reference while said body parts are in said starting orientations and determining the positions of said sensors in said frame of reference when said body parts are in said moved orientations, said steps of transforming and displaying said images including the step of adjusting the positions of said displayed transformed images of said body parts relative to one another to compensate for movement of said body parts relative to one another so that said displayed images correctly represent the positions of said body parts relative to one another.

30. A method as claimed in claim 28 wherein said body parts are bones connected to one another at a common joint.

31. A method as claimed in claim 28 further comprising the steps of providing an instrument probe on a medical instrument and monitoring the orientation of said instrument during said procedure by monitoring magnetic fields transmitted to or from said instrument probe and displaying a representation of said instrument in conjunction with said image of said body part so that the orientation of said instrument representation relative to said displayed image of said body part corresponds to the orientation of said instrument relative to said body part.

32. A method as claimed in claim 31 further comprising the step of determining the positions of said sensors and said instrument probe in said fixed frame of reference while said body part and said instrument are in said starting orientations, determining the positions of said sensors and said instrument probe in said frame of reference when said body part and said instrument are in said moved orientations, said steps of displaying said image and said representation of said instrument including the step of adjusting the position of said representation of said instrument relative to said displayed transformed image of said body part so that said displayed image and representation correctly represent the position of said instrument relative to said body part.

33. Endoscopic apparatus comprising:
(a) means for generating magnetic fields in a field frame of reference so that at least one parameter of said field is quasilinear with respect to distance from point to point within said field frame of reference;
(b) a probe adapted for disposition in the patient's body;
(c) a sensor mounted on said probe for monitoring magnetic field components in at least two different local directions relative to said sensor prevailing at said sensor while said probe is disposed in the patient's body and sending one or more sensor signals representing said components so that said one or more sensor signals including separate data representing each of said components; and
(d) calculation means for determining the position of said probe in said frame of reference from said sensor signals while said probe is disposed in the patient's body and providing probe position data representing the position of said probe in said field frame of reference based upon said sensor signals.

34. Apparatus as claimed in claim 33 further comprising superposition means for displaying an image of the patient's body with an image representing said probe superposed thereon so that the image representing said probe is superposed at a location on said body image dependent upon said probe position data provided by said calculation means.

35. Apparatus as claimed in claim 34 wherein said probe includes an elongated structure having a proximal end and a distal end, said sensor being mounted at said distal end.

36. Apparatus as claimed in claim 35 wherein said probe further includes local imaging means mounted adjacent said distal end of said structure for acquiring an image of body portions surrounding said distal end.

37. Apparatus as claimed in claim 34 wherein said superposition means includes means for accepting body image data representing said body image in a body image frame of reference other than said field frame of reference, means for accepting relationship data representing the relationship between said body image frame of reference and said field frame of reference and means for transforming at least one of said probe position data and said body image data so as to provide said probe position data and said body image data in a common frame of reference.

38. Apparatus as claimed in claim 37 wherein said determination means further includes means for determining the orientation of said probe in said field frame of reference.

39. Apparatus as claimed in claim 34 wherein said means for generating a magnetic field includes means for generating said field so that said at least one parameter varies according to a plurality of different patterns at different times during a preselected sequence of patterns.

40. Apparatus as claimed in claim 39 wherein said means for generating magnetic fields is operative to generate at least one homogeneous field having substantially direction and strength throughout a preselected sensing region and to generate one or more gradient fields each having at least one parameter which varies substantially linearly with distance in said sensing region.

41. A method of operating a probe within a living patient comprising the steps of:
(a) generating a magnetic field in a field frame of reference so that at least one parameter of said field is quasilinear with respect to distance from point to point within said frame of reference;
(b) disposing a probe in the patient's body so that said magnetic field impinges on said probe;
(c) sensing individual components of the magnetic field prevailing at said probe in plurality of local directions relative to said probe while said probe is disposed in the patient's body and sending one or more sensor signals incorporating separate data representing each said component of such magnetic field of said probe;
(d) determining the position of said probe in said field frame of reference from said sensor signals while said probe is disposed in the patient's body and providing probe position data representing the position of said probe in said field frame of reference.

42. A method as claimed in claim 46 further comprising the steps of displaying an image of the patient's body with a representation of said probe superposed thereon so that the representation of said probe is superposed at a location on said body image dependent upon said probe position data and observing said superposed representation to monitor the position of the probe within the patient's body.

43. A method as claimed in claim 42 further comprising the step of monitoring or influencing a condition within the patient's body through said probe.

44. A method as claimed in claim 43 wherein said step of disposing a probe includes the step of inserting said probe into the body of the patient so that said probe is disposed within the brain of the patient and said step of monitoring or influencing a condition includes the step of performing a surgical operation within the brain.

45. A method as claimed in claim 42 wherein said determining step includes the step of determining the orientation of said probe in said field frame of reference from said sensor signals and providing orientation data representing such orientation, said displaying step including the step of superposing said representation of said probe on said image representing the patient's body so that the orientation of said representation of said probe relative to said body image depends upon said orientation data.

* * * * *

UNITED STATES PATENT AND TRADEMARK OFFICE
CERTIFICATE OF CORRECTION

PATENT NO. : 5,558,091
DATED : September 24, 1996
INVENTOR(S) : Acker et al.

It is certified that error appears in the above-indentified patent and that said Letters Patent is hereby corrected as shown below:

Column 2, line 47, "SUMMARY OF THE" should read --SUMMARY OF THE INVENTION--.

Column 4, line 5, "homogeneousfield" should read --homogeneous-field--.

Column 5, line 65, ",aspects" should read --aspects--.

Column 10, line 8, "The" should read --the--.

Column 11, line 1, "biddy" should read --body--.

Column 16, line 36, "$_z$" should read --$_z$--.

Column 16, line 61, "$R_{xx}$ $R_y'_x$" should read --$R_{xx}$ $R_{yx}$--.

Column 16, line 63, "$H'_{xx}$ $H'_{yx}$" should read --$H'_{xx}$ $H'_{yx}$--.

Column 16, line 66, "$R_{x',x}H'$" should read -- $R_{x',x}$-$H'$--.

Column 17, line 2, "$H'_x$" should read --$H'_x$--.

Column 19, line 56, "Thus;," should read --Thus;--.

UNITED STATES PATENT AND TRADEMARK OFFICE
CERTIFICATE OF CORRECTION

PATENT NO. : 5,558,091
DATED : September 24, 1996
INVENTOR(S) : Acker et al.

It is certified that error appears in the above-indentified patent and that said Letters Patent is hereby corrected as shown below:

Column 26, line 58, "having a magnitude" should read --having magnitude--.

Column 29, line 3, "having a magnitude" should read --having magnitude--.

Signed and Sealed this

Eighteenth Day of February, 1997

Attest:

Attesting Officer

BRUCE LEHMAN

Commissioner of Patents and Trademarks